(12) United States Patent
Jovanovich et al.

(10) Patent No.: US 6,551,839 B2
(45) Date of Patent: Apr. 22, 2003

(54) METHOD OF MERGING CHEMICAL REACTANTS IN CAPILLARY TUBES

(75) Inventors: Stevan B. Jovanovich, Livermore, CA (US); Gregory J. Ronan, Palo Alto, CA (US); David J. Roach, Los Gatos, CA (US); Richard F. Johnston, Murphys, CA (US)

(73) Assignee: Amersham Biosciences Corp., Sunnyvale, CA (US)

( * ) Notice: Subject to any disclaimer, the term of this patent is extended or adjusted under 35 U.S.C. 154(b) by 0 days.

(21) Appl. No.: 09/770,412

(22) Filed: Jan. 25, 2001

(65) Prior Publication Data

US 2001/0007641 A1 Jul. 12, 2001

Related U.S. Application Data

(63) Continuation-in-part of application No. 08/927,645, filed on Sep. 11, 1997, now Pat. No. 6,190,616.

(51) Int. Cl.[7] .................................................. G01N 1/10
(52) U.S. Cl. ...................... 436/180; 436/150; 436/164; 435/6; 422/100
(58) Field of Search .................. 435/6, 91.2, 286.5, 435/287.2, 303.1; 436/52, 180, 174, 150, 164, 166; 422/70, 100, 103; 204/450, 451, 453, 600, 604, 601; 137/625.46

(56) References Cited

U.S. PATENT DOCUMENTS

| | | | |
|---|---|---|---|
| 3,071,155 A | 1/1963 | Danley | 137/625 |
| 3,570,314 A | 3/1971 | Wagner | 73/422 |
| 4,027,945 A | 6/1977 | Iverson | 350/96 C |
| 4,401,365 A | 8/1983 | Mizokawa et al. | 350/96.2 |
| 4,445,391 A | 5/1984 | Cabrera | 73/864.12 |
| 4,448,214 A | 5/1984 | D'Alessio | 137/625.46 |
| 4,472,052 A | 9/1984 | Lofgren | 356/44 |
| 4,492,427 A | 1/1985 | Lewis et al. | 350/96.2 |
| 4,507,977 A | 4/1985 | Cabrera | 73/864.12 |
| 4,632,149 A | 12/1986 | Oroskar et al. | 137/625.15 |
| 4,641,915 A | 2/1987 | Asakawa et al. | 350/96.18 |
| 4,677,844 A | 7/1987 | Sonoda | 73/55 |
| 4,702,889 A | 10/1987 | Cabrera et al. | 422/103 |
| 4,726,929 A | * 2/1988 | Gropper et al. | 356/244 |
| 4,726,932 A | 2/1988 | Feier et al. | 422/103 |
| 4,822,569 A | 4/1989 | Pellegrino | 422/103 |
| 4,948,565 A | 8/1990 | Bemis et al. | 422/103 |
| 4,953,932 A | 9/1990 | Mihich | 350/96.15 |
| 5,127,429 A | 7/1992 | Kempf et al. | 137/240 |
| 5,158,751 A | 10/1992 | Del Valle et al. | 422/103 |
| 5,179,606 A | 1/1993 | Kihara et al. | 385/45 |
| 5,207,643 A | 5/1993 | Davis | 604/80 |
| 5,217,045 A | 6/1993 | Gramm | 137/595 |
| 5,250,263 A | 10/1993 | Manz | 422/81 |
| 5,288,113 A | 2/1994 | Silvis et al. | 285/342 |
| 5,383,493 A | 1/1995 | Brandauer et al. | 137/625.46 |
| 5,453,170 A | 9/1995 | Krstanovic et al. | 204/299 R |
| 5,458,761 A | 10/1995 | Kamahori et al. | 204/299 R |
| 5,480,614 A | * 1/1996 | Kamahori | 204/603 |
| 5,487,569 A | 1/1996 | Silvis et al. | 285/24 |
| 5,492,555 A | 2/1996 | Strunk et al. | 95/86 |
| 5,494,641 A | 2/1996 | Krstanovic | 422/103 |
| 5,496,460 A | 3/1996 | Jorgenson et al. | 204/604 |
| 5,534,707 A | 7/1996 | Pentoney | 204/452 |
| 5,540,464 A | 7/1996 | Picha | 285/328 |
| 5,573,651 A | * 11/1996 | Dasgupta et al. | 204/601 |
| 5,588,077 A | 12/1996 | Woodside | 385/26 |
| 5,615,291 A | 3/1997 | Hayakawa et al. | 385/84 |
| 5,682,452 A | 10/1997 | Takahashi | 385/85 |
| 6,130,098 A | * 10/2000 | Handique et al. | 422/100 |

FOREIGN PATENT DOCUMENTS

JP 07-107962 A * 4/1995

* cited by examiner

*Primary Examiner*—William H. Beisner
(74) *Attorney, Agent, or Firm*—Thomas Schneck; David M. Schneck

(57) ABSTRACT

A capillary valve, connector and router where one or more cylindrical fibers, which may be capillaries, plugged capillaries, optical fibers, or the like, including at least one capillary tube are contained in a first bundle of fibers that terminates at a first face. A second cylindrical bundle of fibers also containing one or more fibers including at least one capillary tube terminates in a second face abutting the first face. A fastener or adapter holds the members together with faces in mutually biased alignment. Connection of a plurality of macroscale pumps enables push-pull fluid motion, with routing, in a capillary system formed by a plurality of fibers coupled by switches, connectors and routers. Chemical reactions, separations and analysis may be carried out with microliter volumes or smaller.

10 Claims, 13 Drawing Sheets

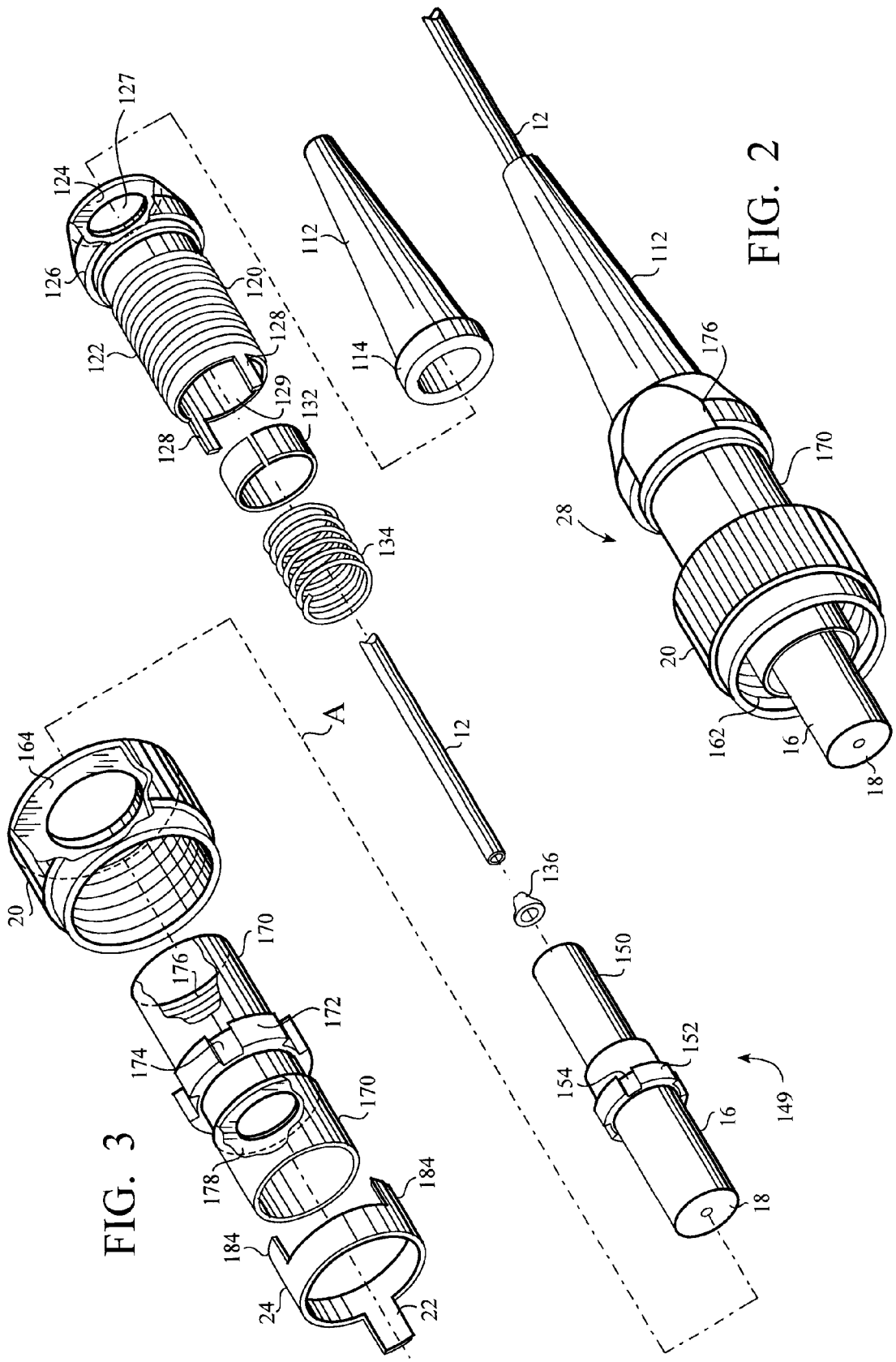

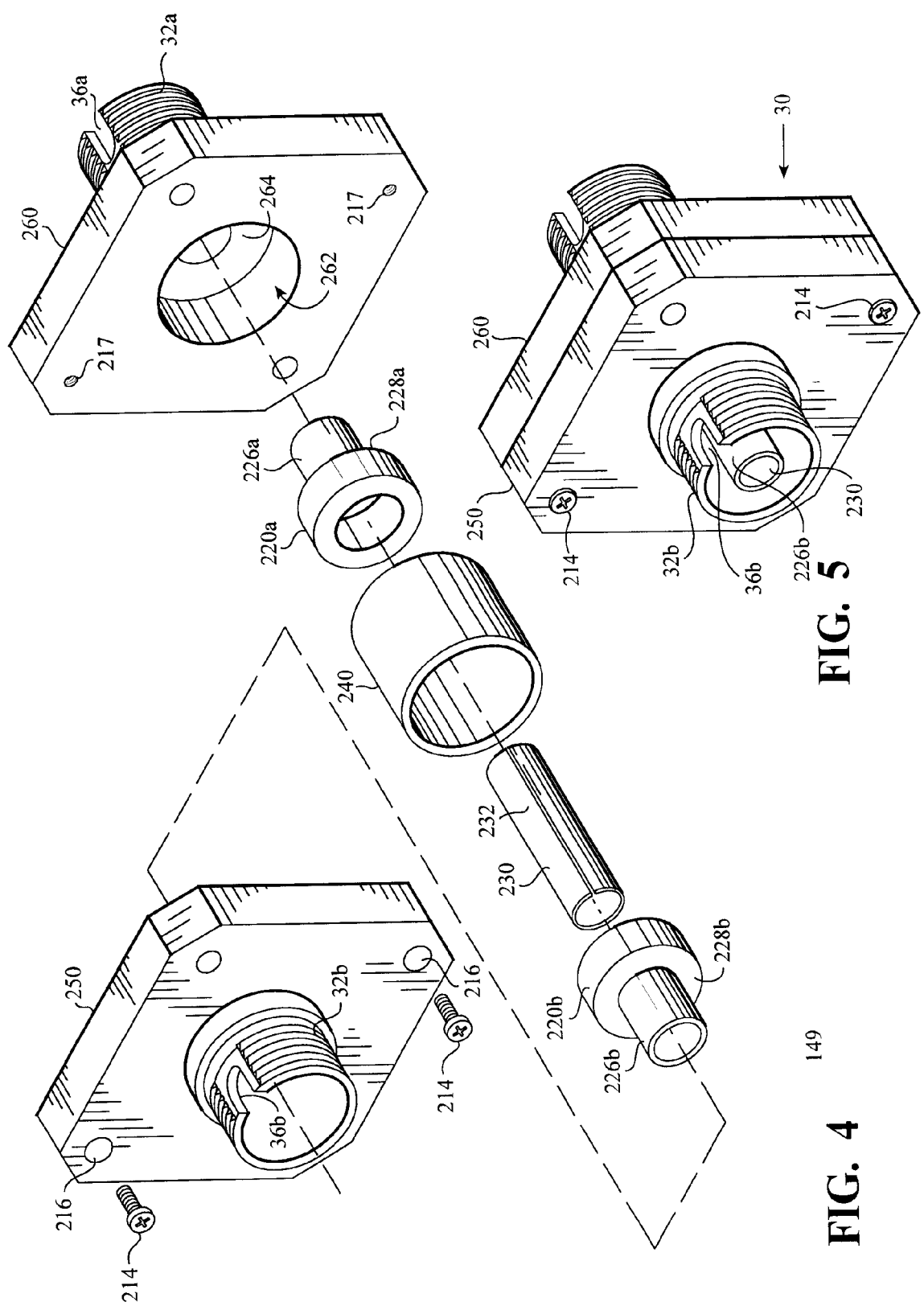

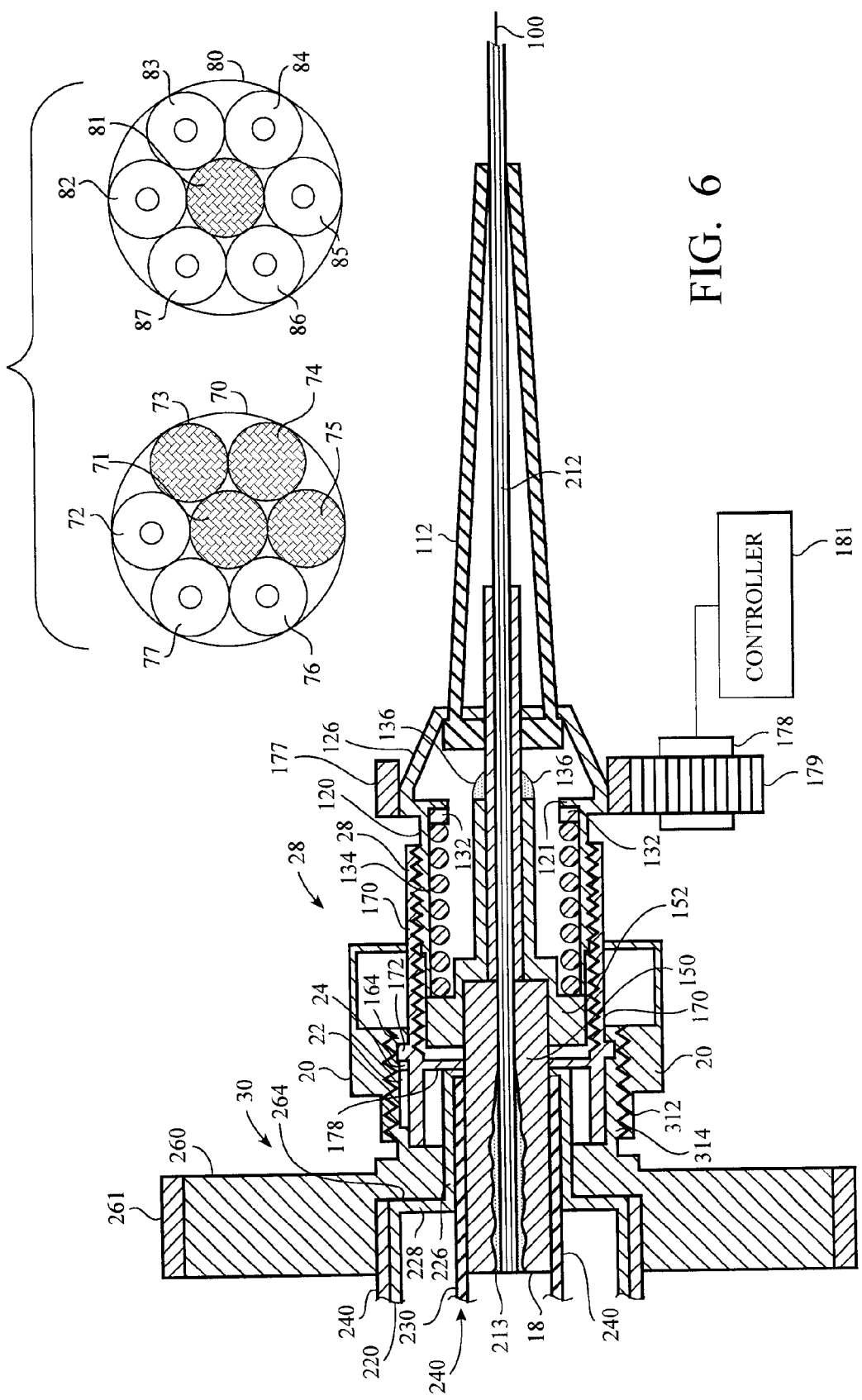

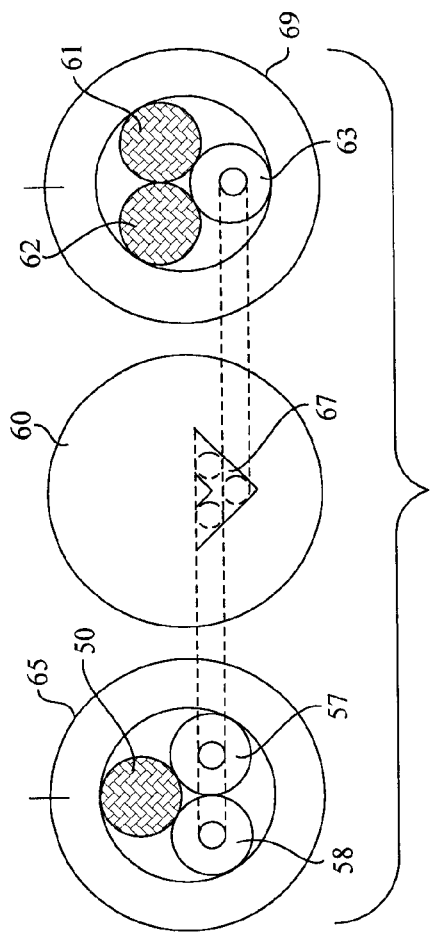
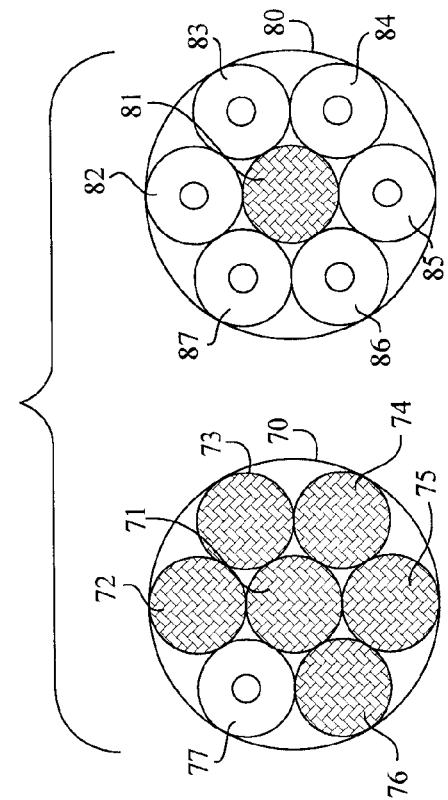
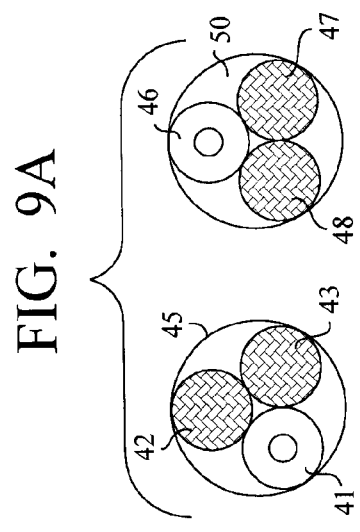
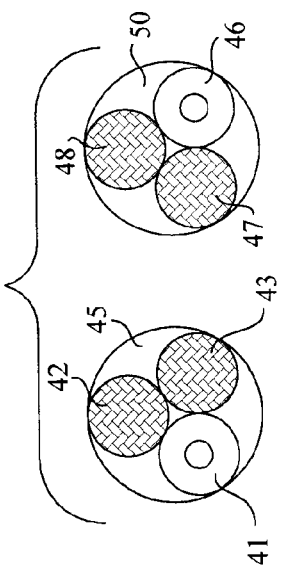
FIG. 10
FIG. 11
FIG. 9A
FIG. 9B

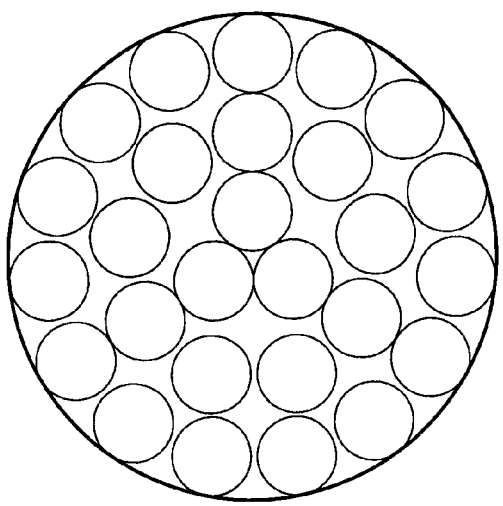
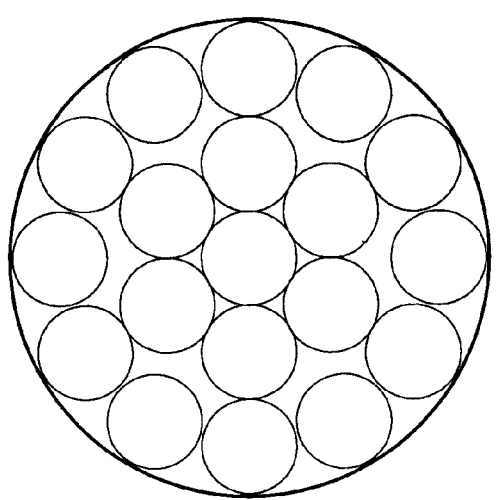
FIG. 17a　　　　　　FIG. 17b
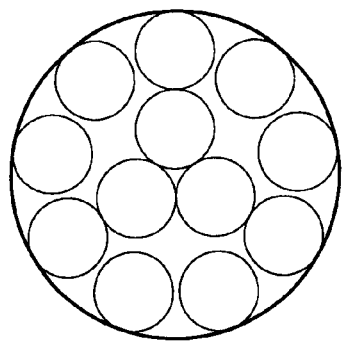
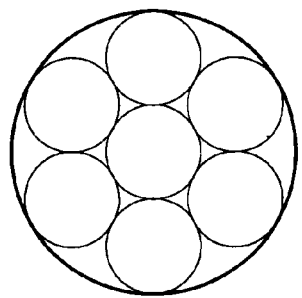
FIG. 17c　　　　　　FIG. 17d
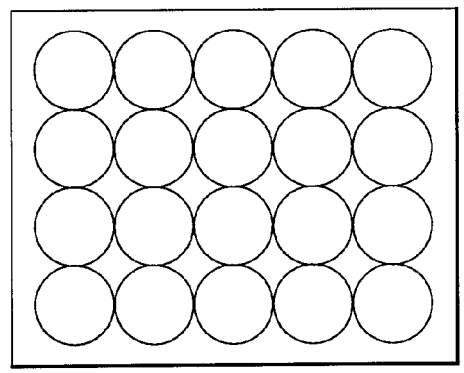
FIG. 17e

METHOD OF MERGING CHEMICAL REACTANTS IN CAPILLARY TUBES

CROSS-REFERENCE TO RELATED APPLICATION

This application is a continuation-in-part application of Ser. No. 08/927,645 filed Sep. 11, 1997, now U.S. Pat. No. 6,190,616.

FIELD OF THE INVENTION

This invention relates generally to capillary valves and devices for interconnecting capillary tubes with each other, with microfabricated devices, and macroscale devices.

BACKGROUND OF THE INVENTION

Capillary tubes are useful in a wide range of microfluidic applications, particularly where volumes on the order of a microliter or smaller are handled. Capillaries are made of glass, metal, silica, or a polymer. The outer diameter of a capillary tube ranges from under 100 to over 750 microns. The diameter of the inner bore ranges from 2 to over 500 microns. With only minimal amounts of chemicals required, systems utilizing capillary tubes are well suited for producing high sample throughput with minimal use of space and materials. In electrophoretic applications, the high surface to volume ratio of capillaries enables the use of high voltages with low joule heating. The use with high voltages results in the ability to electrophoretically separate compounds in capillary tubes at several times the speed and resolution available with traditional slab electrophoretic separation.

Numerous applications have developed to take advantage of the benefits that capillary tubes provide. For example, one use of capillary tubes is in microfluidic devices where capillary tubes are used to transport small amounts of fluid from one location to another. Another application using capillary tubes entails temporarily sealing both ends of a capillary tube to form a nanoscale reaction vessel. Finally, chromatographic devices utilize capillary tubes to provide a separation column for substances. The substances can then be separated based on their physical properties, such as mass, size, or shape. Such applications include gas chromatography and liquid microbore chromatography.

All of these applications require that sections of capillaries be connected to each other. For example, gas chromatography will require an injection port that can introduce a sample into a flow stream. The varied uses of capillary tubes require capillary connectors that are both versatile and resilient. The physical stresses placed on these capillary connectors are most demanding. The connector must be inert to reactive substances that flow through the capillaries, including organic solvents. The connector must remain leak free when used to contain a liquid, gas, or a fluid separation matrix at pressures ranging from 0 to 10,000 PSI.

In high electric voltage applications, the connector must be insulated from these voltages, which can be over 10,000 volts. The connector should add negligible additional volume to the capillary column to avoid degrading separation resolution in electrophoretic applications. In addition, the connector should be able to act as an interface for connecting macroscale devices (such as injectors, fluid reservoirs, or sample depositors) to microscale capillary tubes. Finally, to aid in the simple manipulation of the connector, the connector must be reusable and simple to connect. The varied uses of the connector in a number of applications require that the connector serve several different functions. Primarily the connector must be able to serve as a leak free, high pressure connector for two or more capillary tubes. The connector should provide a number of other functions as well. The connector could serve as a valve, enabling both the ability to close an end of a section of capillary tubing and the ability to route fluid from one capillary tube into a selectable second capillary tube. In addition, it would be useful for the connector to function as a manifold enabling the combination of the flow streams from a plurality of input capillary tubes to channel into a single output capillary tube or splitting a flow stream from a single capillary tube into multiple flow streams in multiple capillary tubes. The connector preferably would have negligible dead space volume, both as a connector and as a valve. Finally, the connector should enable connection of macroscale devices to microscale capillary tubes.

By combining these features within one connector, a multitude of uses become a possible. By using two such connectors at the two ends of a section of capillary tubes, a reversibly sealable nanoscale reaction chamber is formed. If the first connector also functions as a manifold, a plurality of input lines could flow into this nanoscale reaction chamber before it is sealed to allow for mixing a number of chemicals in the reaction. If the output line also functions as a manifold, once the reaction is complete, the mixture could be divided into multiple lines for sending flow streams to multiple analytical devices or to a waste reservoir.

In the past, several couplers have been developed to attach together the ends of capillary tubes. Some capillary connectors employ a ferrule with a longitudinal bore therethrough for inserting the ends of the capillaries to be coupled together and a compression fitting for mechanically compressing the ferrule to seal the connector. U.S. Pat. No. 5,288,113 to P. H. Silvis et al. teaches a heat-resistant connector for releasably joining end portions of two capillary tubes in end-to-end fashion for use in chromatography. U.S. Pat. No. 5,540,464 issued to Picha, describes a capillary connector where the ends of a capillary tube are press fit into a resilient member with a tapering throughbore. A split sleeve holds a pair of these members together in mutually facing alignment, with the throughbore aligned to enable two capillary tubes to come into fluid communication. U.S. Pat. No. 5,453,170 to S. Krstanovic et al. teaches coupling a capillary to a fine wire electrode to form an ion detector.

Some of the capillary connectors demonstrate the ability to couple together more than two capillaries. U.S. Pat. No. 5,487,569, issued to Silvis et al., teaches a glass insert with a plurality of legs connected at a central portion. Each leg has a tapered inner bore that receives one end of a capillary tube. On each of these legs is annularly mounted a connecting member containing a sealing ferrule for making a seal between the capillary and the leg. U.S. Pat. No. 5,494,641, issued to Krstanovic, describes a system for connecting any number of capillary tubes into a system by mounting the capillary tube within a cavity in a mechanical fastener. The capillary tube can then be attached to any apparatus that has been adapted to accept the fastener.

These capillary connectors function to link sections of capillary tubes. It would be advantageous to have a connector that could serve other functions.

Currently, there are several devices that have been used as valves or gates for capillaries. One capillary valve requires that the capillary tubes be attached to holes in a thin wafer, such as a silicon wafer. A flexible membrane is positioned on the opposite side of the wafer. By exerting pressure on the membrane, the membrane is pressed against the holes in the silicon wafer and the valve is closed. U.S. Pat. No. 5,492,555, issued to Strunk et al., describes a two dimensional capillary gas interface. One part of the device is a bimodal six way capillary valve. This valve comprises a cylindrical section with a longitudinal axis perpendicular to the plane containing the longitudinal axis of three sections of capillary tubes. The valve operates by rotation of the cylindrical section to align the ends of the capillary tube in the tangential plane of the cylinder with the ends of other capillary tubes bringing the section into fluid communication. Further rotation will bring the ends of the capillary tubes in the rotating cylindrical section out of communication with the capillary tubes, closing the valve. This valve has significant dead volume of several microliters.

The inner diameters of capillary tubes must connect to devices that are an order of magnitude or more larger. This has been a persistent problem for the field of microfluidics. Some attempts have been made to provide for a macroscale to microscale interface. For example, capillary tubes have been attached to pressurized reservoirs. An inlet to the reservoir is capped by a rubber septum. A macroscale injector, such as a syringe, can introduce a sample into the reservoir, and the sample will be pressure driven into the capillary tube. After repeated injections through the septum, the septum will no longer remain pressure tight and will require replacement.

Both the connectors and the valves presently available are not ideal. None of these devices combine in one connector the ability to connect a number of capillaries, but also to act as a zero dead volume valve, or as a manifold, or as a router of fluid. As noted above, such a connector would greatly enhance the utility of many systems that use capillary tubes. Furthermore, no device presently available is an adequate interface between macroscale and microscale devices. An object of the invention was to provide improved connectors and valves for capillaries and to connect macroscale devices with macroscale devices.

SUMMARY OF THE INVENTION

The above object has been achieved with a capillary connector, which is able to join into fluid communication a plurality of capillary tubes, but also can function as a valve, a fluid router, a manifold, a reaction chamber and a macroscale to microscale connector. Each connector is simple in design and is rapidly and easily connected and disconnected. The connector has negligible dead volume whether functioning as a capillary tube connector, a valve, a fluid rotor, a manifold, a reaction chamber or a macroscale-to-microscale connector. The basic connector consists of two members, with each member consisting of the same basic parts. Each member includes an input bundle of fibers, which are usually capillaries, entering the member, with the input bundle terminating in a ferrule rotatably attached to the member. The input bundle is a set of one or more axially parallel, packed cylinders or fibers, at least one of which is usually a capillary tube, but which also can include non-hollow fibers, such as plugged capillaries, electrodes and fiber optical fibers. The fibers terminate at the end of the ferrule. A fastener connects these two members and holds the ends of the ferrules in mutually biased axially parallel alignment. The rotatable ferrules can then be rotated in relation to each other. The fibers packed within the ferrule would be affixed within the bundle and ferrule and be relatively non-rotating in relation to the bundle and ferrule. By rotation of the ferrules, the rotational orientation of the fibers about an axis in the first bundle would be altered in relation to the orientation of fibers about the same axis in the second bundle, but the axially parallel alignment would remain.

Each member of the connector could have an indicator to indicate the rotational orientation of each ferrule. In one embodiment, the indicators consist of a mark or notch on the ferrule above the centered location of a capillary tube. Alignment of the marks on the two ferrules would indicate that corresponding capillary tubes within the ferrules were aligned and in fluid communication. In another embodiment, optical fibers are used to align the rotation of the capillary connector.

With this basic connector, several different functions are possible. The connector can function to put two corresponding capillary tubes into fluid alignment and thus function as a basic connector. Unlike other available connectors, this connector would also function as a connector between macroscale devices and microscale capillary tubes. It can also function to connect multiple capillaries in one member to a second member with either an equal number of capillaries or with an unequal number of capillaries or only a single capillary.

In addition, the connector can function as a valve. When the ends of the capillaries in both ferrules are aligned, the valve is open. If the ferrule of the second member is rotated in relation to the orientation of the first ferrule, the ends of the capillary tubes can be displaced in relation to each other so that non-corresponding solid cylinders, which may be glass fibers, metal, plastic or a plugged capillary, are aligned with the capillaries and the ends of the capillary tubes will be blocked or closed. These cylinders are generally referred to as non-hollow fibers and plugged capillaries, since these are preferred elements, the main consideration being an outer diameter which is the same as a corresponding capillary which it faces at a ferrule-to-ferrule interface. In other words, when non-hollow fibers are contained within the ferrule of a first connector member, the flow within a capillary could be blocked by orienting the ferrule of a second connector member such that the end of the capillary of the second connector member and the end of the non-hollow fiber of the first connector member are in alignment. The valve is also closed whenever the ends of the capillaries are not aligned with capillaries on the opposing member, including when the ends are aligned with the inter-capillary surfaces. This valve that is created has essentially no dead volume and is simple to manipulate by rotation. The alignment marks, fibers, or scale or notches on the ferrules would indicate if the valve is open or closed. A calibrated scale will allow partial blockage of a capillary by incomplete overlap with the open end of a capillary. If the non-hollow fibers are fiberoptic fibers, alignment could be indicated by passing light through the fibers and detecting if the light passes through a distal end of the fiber. This rotatable valve can also function as a router. For example, if capillaries aligned on ferrules of both members are rotated such that capillaries on a first member now align with different capillaries on the second member, a router is created. Similarly, depending on the application, some capillaries on the first member can be routed to capillaries on the second member, while other capillaries are closed.

Typically, rotation of the ferrule is effected by manual operation. It is also possible to operatively associate the ferrule with a motor to effect automated controlled rotation of the ferrule. The motor would operate in accordance with instructions from a controller that a user would program to give desired results. The orientation of the ferrules would then be automatically controlled with precision timing for volumetric accuracy, especially if variable blockage of a capillary is implemented.

The basic connector, comprised of the two connector members mutually biased against each other, readily transforms into a manifold. This would require that one of the ferrules be associated with a bundle of packed capillary tubes and the second ferrule be associated with a bundle containing one capillary tube. Between these two ferrules would be placed a washer with a cut out pattern. The cut out pattern would bring into fluid communication the flow streams of the plurality of tubes in the first ferrule with the inner bore of the single capillary in the second ferrule. The same result could also be achieved by slightly recessing the capillary tube in one ferrule and having a groove extend between the recessed capillary tubes. This would allow the inner bore of the capillary tube in the second ferrule to come into fluid communication with the first set of capillary tubes. Alternatively, a plurality of capillary tubes in one bundle and ferrule can be associated with a single capillary tube in another bundle and ferrule whereby the inside diameter of the single capillary is large enough to encompass more than one capillary tube in the other ferrule.

This basic connector is adaptable for many different uses. By placing oppositely charged electrical leads on the opposite sides of connector members and filling the tubes with a conducting media, the media will conduct electricity without shorting on the connectors. This enables capillary electrophoresis reactions, electroosmotic pumping or other applications of electrical forces to be performed in the tubes joined by these connectors.

In addition to the use of the present invention wherein two connector members are joined together, the invention also can be used as a single connector member that could be joined to any other device that contains a port member to receive the connector member. This connector member would be comprised of a rotatable ferrule containing at least one capillary tube terminating at a substantially level surface. An alignment indicator on the ferrule, such as a mark or notch, would indicate the orientation of the capillary tubes within the ferrule. The member would have an attachment device, such as an annular nut, capable of attaching to a mating mount, such as a threaded protrusion of a receiving well. This would allow a capillary to be joined to any of a variety of port members, including microfluidic attachments to microchips or attachment to a port member of a moveable arm for the deposition of an array of spots on a surface. The moveable arm would allow placement of such spots in different locations. By including multiple capillary tubes within the ferrule, the connector member could mix compounds on a spot or could be attached to a receptacle for deposition of the reactants to be mixed.

BRIEF DESCRIPTION OF THE DRAWINGS

FIG. 2 is a perspective view of a single connector member shown in FIG. 1.

FIG. 3 is an exploded perspective view of a connector member shown in FIG. 2.,

FIG. 4 is an exploded perspective view of the fastener shown in FIG. 1.

FIG. 5 is a perspective view of the fastener member shown in FIG. 4.

FIG. 6 is a side cutaway view of an alternate embodiment of a single connector member joined to a fastener.

FIGS. 9a and 9b are schematic sectional views showing non-rotatable fibers at ends of rotatable ferrules of the type shown in FIG. 7 function as a valve.

FIG. 10 is a schematic sectional view showing ferrules of the type shown in FIG. 7 combined with a washer functioning as a manifold.

FIG. 11 is a schematic sectional view of two rotatable ferrules of the type shown in FIG. 7 functioning as a fluid router.

FIG. 11a is a schematic sectional view of two rotatable ferrules of the type shown in FIG. 7 functioning as a fluid router.

FIGS. 17a–17e are schematic sectional views of ferrules with multiple fibers in closely packed geometric arrangements.

BEST MODE OF CARRYING OUT THE INVENTION

Figure 1:
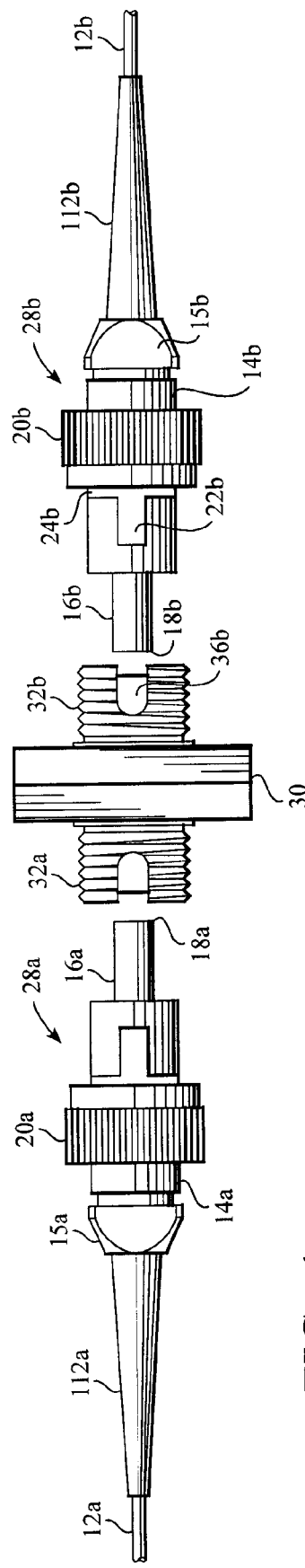
FIG. 1 is a side view of two connector members and a fastener for the members according to the present invention.

With reference to FIG. 1, a connector is adapted from a standard FC-style fiber optic connector, consisting of a first connector member 28a and a second connector member 28b joined by an adapter 30. The first connector member 28a has a first capillary 12a entering a ring 14a and extending into rotatable ferrule 16a. The capillary 12a is fixedly attached within rotatable ferrule 16a and terminates at end 18a of rotatable ferrule 16a. The end may be flat or, more typically, have a slight radius.

In a similar manner, in the second connector member 28b a second capillary 12b enters a ring 14b and extends into rotatable ferrule 16b. The capillary 12b is fixedly attached within rotatable ferrule 16b and terminates at end 18b of rotatable ferrule 16b.

An adapter 30 located between the two connector members 28a and 28b join the two connector members. Rotatable ferrule 16b is mounted into externally threaded cylindrical protrusion 32b. The orientation of an internally threaded knurled nut 20b in relation to externally threaded cylindrical protrusion 32b is determined by key 22b extending from key ring 24b which is coaxial with capillary 12b. Key 22b fits into gap 36b in externally threaded cylindrical protrusion 32b. Knurled nut 20b is rotated about externally threaded cylindrical protrusion 32b to securely attach connector member 28b to adapter 30. In a similar manner, rotatable ferrule 16a is mounted into externally threaded cylindrical protrusion 32a. Knurled nut 20a is rotated about externally threaded cylindrical protrusion 32a to securely attach connector member 28a to adapter 30.

When connector members 28a and 28b are joined together, the ends 18a and 18b are pressed together within adapter 30. The capillaries 12a and 12b can then be brought into alignment if symmetrically affixed within ferrules 16a and 16b.

A ferrule 16a can terminate a set of one or more fibers. This set of one or more fibers can be a single capillary tube or can be a plurality of fibers, at least one of which is a capillary tube. The capillary tube is made of glass, silica, metal, polymer, or other materials. In the preferred embodiment, any non-hollow fibers included are fiber optic fibers or capillaries that have been plugged with material, such as epoxy.

Strain relief boots 112a and 112b are preferably included extending from and mounted within faceted heads 15a and 15b of knurled cylinders 20a and 20b to prevent mechanical stresses from bending or breaking the fibers contained within cylindrical sleeves 12a and 12b.

FIG. 2 shows a connector member 28 as assembled. A capillary 12 enters connector member 28 passing through strain relief boot 112, through connector 170 and terminating at end 18 of ferrule 16. Nut 20 is annularly disposed about connector 170.

FIG. 3 shows coaxial component parts for assembling one of the connector members 28a or 28b along an axis A. The strain relief boot 112 is inserted into an end of externally threaded hollow bolt 120. The annular exterior lip 114 of boot 112 is secured against the annular interior lip 124 of faceted head 15. Once boot 112 is inserted into bolt 120 a compression ring 132 is inserted into bolt 120 at opening 129 and slid to the head end of bolt 120. Compression ring 132 will fit tightly into bolt 120. Next spring 134 is slid into opening 129 of bolt 120 and rests on a shoulder inside of connector body 170.

Capillary 12 extends into head opening 127 of hollow bolt 120 and passes through bolt 120 and into ferrule 16. The capillary terminates at end face 18 of ferrule 16. Epoxy 136 holds the capillary 12 in place at the end face 18 of ferrule 16.

Ferrule 16 is typically a metal or ceramic cylindrical body having an axial hole into which the capillaries or fibers are secured in place. The ferrule is either press fit or epoxied into ferrule stem 150. Ferrule 16 has an outer diameter tolerance of minus zero, plus one micrometer. The hole is axially bored to an axial tolerance ranging between 2 to 15 micrometers, depending on capillary diameter and number of capillaries. The space between capillaries is filled with epoxy. The annular flange 152 is notched with notches 154. Four notches are disposed about annular flange 152 with each notch being equally separated.

Knurled nut 20 is fit over the assembly of hollow bolt 120. Hollow cylinder 170 is then fit over ferrule 150 and inserted inside knurled nut 20. An annular flange 172 on hollow cylinder 170 fits against annular interior lip 164 on knurled nut 20. Hollow cylinder 170 then extends over ferrule 150 with interior annular lip 178 forced against annular flange 152. Cylinder 120 is rotated onto the mating interior threads 176 of cylinder 170. As cylinder 170 is fully tightened down onto bolt 120, internal annular lip 178 is forced against annular flange 152 on ferrule 150 forcing the opposite side of flange 152 against spring 134. The tabs 128 extending from the rim of opening 129 on bolt 120 will fit into the notches 154 in annular flange 152, holding ferrule 150 rotationally secure. As cylinder 170 is fully tightened, spring 134 will compress, pressing against annular flange 152 and biasing ferrule 150 from within bolt 120 with about twenty grams of force.

A key ring 24 with a key 22 is fit over hollow cylinder 170 and the two prongs 184 fit into two of the six notches 174 disposed about annular flange 172.

Several methods exist for rotating the orientation of the ferrule. First, by rotating the ferrule assembly 149 one quarter turn, a new pair of notches 154 will align with prongs 128. This enables four different orientations of ferrule 150. In addition, by rotating key ring 24 in relation to cylinder 170 different notches 174 on annular flange 172 will align with ring prongs 184. The annular flange 172 has six notches 174 disposed about the flange. The enables six different orientations of the ferrule 150 position relative to the key 22.

In an alternative embodiment, key ring 24 is made without ring prongs 184, or the key ring 24 is not used. This would result in a cylinder that is may be freely rotated in the adaptor. By turning the hollow bolt 120, ferrule assembly 149, which is non-rotatably held within the assembly of hollow bolt 120 and hollow cylinder 170, would then also rotate, altering the orientation of the non-rotating end fibers epoxied into ferrule 150.

FIG. 4 shows the component parts for assembly of adapter 30. The rear faceplate 260 has a cylindrical indentation 262 and an annular lip 264. Rear hub 220a fits within rear faceplate 260 with the annular lip 226a on hub 220a fitting against lip 264 with hollow cylindrical protrusion 226a on hub 220a extending beyond the lip and into exteriorly threaded cylindrical protrusion 32a on rear face plate 260. Cylinder 240 coaxially aligns hub 220a and hub 220b. Into hollow cylindrical protrusion 226a of rear hub 220a split zirconia sleeve 230 is inserted, with sleeve extending to near the end of cylinder 226a, stopped at a lip therein. Front hub 220b fits into the other end of cylinder 240 and the other end of sleeve 230 fits into cylindrical protrusion 226b. Front face plate 250 fits to rear face plate 260. Cylinder 240 fits within front face plate 250 and cylindrical protrusion 226b extends through face plate 250 into cylindrical protrusion with exterior threading 32b. Screws 214 insert into holes 216 on front face plate 250 and screw into holes 217 on rear faceplate 260.

FIG. 5 shows the assembled adapter 30. Screws 214 have been inserted through front face plate 250 to attach it to rear face plate 260. Alternatively, other forces may be applied to keep face plates 250 and 260 together. The face plates could be rounded to form a driven gear for rotation by a motor discussed below. Cylindrical protrusion 226b extends through face plate 250. Fitted within protrusion 226b is split zirconia sleeve 230. Sleeve 230 is a loose fit inside of hubs 220a and 220b. Exteriorly threaded cylindrical protrusion 32b extends from the center of the fastener.

The fitting of adapter 30 with connector member 28 is shown in FIG. 6. In FIG. 6, a bundle of fibers 212, at least one of which is a capillary, enters the connector through stress relief boot 112 and proceeds into hollow bolt 120. The epoxy coating 213 is only one to a few microns thick. Within the hollow bolt 120, bundle of fibers 212 is attached within ferrule 150 by epoxy 213. The ferrule terminates at face 18. The end faces of the ferrules have a spherical shape, i.e. radiused, to further ensure a leakproof joint. A typical radius of curvature is 5–30 mm. By curving the end faces, the requirements for polishing the end faces are greatly reduced. The end faces are polished such that the central portion of the end face 18, containing the capillaries, comes in contact before the outer portion of the end face. This eliminates the need to polish a flat end face to 0° perpendicularity to the capillary. Non-zero degree end face polish would cause an air gap, leading to leakage.

Ferrule 150 has a circular annular flange 152 which is held against cylinder lip 178 and biased against lip 178 by spring 134. The spring is held in threaded cylinder 120 by compression ring 132. Compression ring 132 is held in place by annular bolt head lip 121.

Internally threaded cylinder 170 is screwed to hollow bolt 120. The interior of cylinder 170 has an annular lip 178 that holds circular flange 152 of ferrule 150. On the exterior of cylinder 170, an annular circular flange 172 abuts annular lip 164 of knurled nut 20. Nut 20 screws onto an exteriorly threaded cylindrical protrusion 32 on rear face plate 260.

On rear face plate 260, cylinder 240 is mounted annularly to hub 220 with hub lip 228 abutting rear face plate lip 264. Cylindrical protrusion 226 extends through rear face plate 260. Mounted within cylindrical protrusion 226 is split zirconia sleeve 240. Zirconia sleeve 240 acts as a spring to align outer diameters of ferrules 150. Inside zirconia sleeve 240 frictionally fits ferrule 150 with the bundle of fibers 212. With nut 20 tightened as shown, the connector member and fastener are securely attached together, and the spring is compressed, thereby compressing end faces, creating a leakproof joint. Typical spring force when fully assembled is two pounds.

A stepper motor 178 may be used to rotate a gear 179, turning meshing gear 177 to rotate ferrule 150 through external teeth on a fully round nut 126 or on a round adapter member 260 having external gear teeth 261, which may be moved by a gear 179. Motor 178 may operate under control of an automatic controller 181 which is programmed to achieve desired valve settings at desired times. The controller allows selectable alignments of a first ferrule relative to a second ferrule.

With this basic connector, a number of uses become possible. As mentioned above, the bundle of fibers 212 contains at least one capillary tube. In one embodiment of this invention, each of the two abutting ferrules of a connector contain three fibers. By rotating these two ferrules in relation to each other, the fibers within the ferrule would be brought into or out of alignment. A non-hollow fiber, typically a plugged capillary tube, could be brought into alignment with a capillary tube, effectively blocking flow through the tube. This would allow the connector to act as a switch. By having one member of the connector contain a bundle of fibers having multiple capillary tubes and the second member contain a bundle of fibers with one capillary, a 3-to-1 fluid router is formed. If a channeling device is located between a ferrule containing multiple capillary tubes and a ferrule containing a single capillary tube, a manifold is formed. Finally, the connector can be used as an interface between macroscale devices and microscale capillary tubes.

Figure 7:
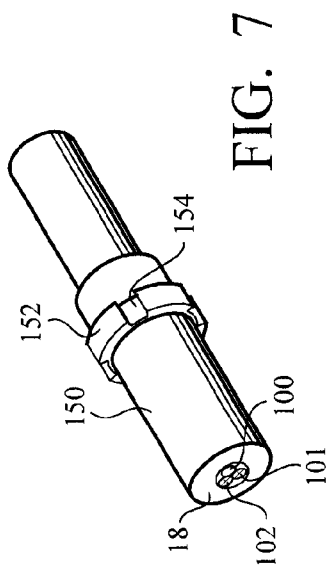
FIG. 7 is a perspective view of a portion of a ferrule for a connector member of the type shown in FIG. 1.

FIG. 7 shows a rotatable ferrule 150. The ferrule is adapted from a FC-style fiberoptic connector. At tip 18 of ferrule 150 the ends of three fibers are seen. These fibers are a capillary tube 100 and two fiber optic fibers, 101 and 102. The capillary and the fibers should have the same outside diameter for closest packing. To adapt the invention from the FC-style connector, a FC-style connector is modified by precision drilling of the ferrule to produce a hole within a few microns of the size of the bundle of fibers. Within a FC-style connector, the bundle of capillaries can contain a single capillary, three capillaries, seven capillaries (packed with one central capillary and 6 radial capillaries), or nineteen capillaries (packed with twelve capillaries surrounding six capillaries surrounding one capillary), or any symmetrical arrangement of fibers or capillaries. Any of the capillaries can be replaced with either a plugged capillary or a fiber optic fiber of equal outside diameter. Asymmetrical arrangements of the fibers with microfabricated adaptors are also possible.

To make a three fiber FC-style connector, the hole of a FC-style connector is either fabricated to accommodate the exterior diameter of a bundle of three fibers or alternatively is drilled or otherwise retrofitted to accommodate the exterior diameter of a bundle of three fibers. The three-fiber bundle is inserted and centered where the bundle consists of three capillaries, the capillaries are inserted and secured in place with epoxy with the ends of the capillaries protruding from the face of the ferrule. The end of the capillaries is then polished back with a slight radius.

Figure 8:
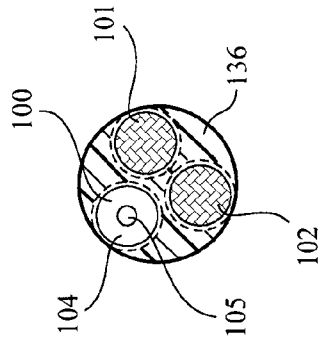
FIG. 8 is an end view of the ferrule shown in FIG. 7.

FIG. 8 shows the end of a ferrule after one unplugged capillary and two plugged capillaries have been inserted and secured in place. A band of epoxy 136 extends axially and secures the capillary tubes in place. A capillary tube 100 with an interior bore 105 and two plugged capillaries 101 and 102 terminate at the end of the ferrule 18. The material comprising the unplugged capillary tube 100 and the plugged capillaries 101 and 102 has been polished back with a slight radius.

This basic embodiment of this invention is readily useable as a zero dead-volume slide valve. A schematic for the connector performing this function is shown in FIGS. 9a and 9b. FIG. 9a shows a representation of the connector when closed. A first ferrule section 45 and a second ferrule section 50 are shown. In the connector, fiber ends, i.e. capillaries, would be in facing alignment and biased against each other in the fastener of the connector. Both of the sets of fibers within the ferrule are offset from the center and precisely mounted with a standardized orientation on the ferrule. This is effected such that plugged capillary 42 in ferrule section 45 could align with capillary tube 46 in ferrule section 50. In a similar manner, plugged capillary 43 in ferrule section 45 would align with plugged capillary 48 in ferrule section 50 and capillary tube 41 in ferrule section 45 would align with plugged capillary 47 in ferrule section 50. Because the two capillary tubes are aligning with non-hollow fibers, no fluid would be able to pass through either of the capillaries and all capillaries in this valve would be closed. The valve could be opened by rotating ferrule section 50 with a one-third turn. This results in the orientation shown in FIG. 9b. Now capillary tube 41 in ferrule section 45 would align with capillary 46 in ferrule section 50. Fluid would then be able to flow through from one capillary to the other. Plugged capillaries 42 and 43 in ferrule section 45 would align with fibers 48 and 47 in ferrule section 50 respectively.

The methods of rotating the ferrules were set out above. When the ferrule is rotated, there needs to be some indication of the alignment of the fibers within the sleeve. This would allow the user to determine if the valve was in an open or closed position.

A first indicator of the orientation of the fibers within a sleeve would be to use markings or notches on hollow cylinder 120. The marking could be located near the end 15 of hollow bolt 120.

When two members of the connector are secured together, the markings on the two cylinders of the two members could indicate the orientation of the fiber bundles secured within the connector. This would indicate the orientation of the fibers located inside the bundles.

A second method of determining alignment would be through the use of optical properties of the fiber optic fibers. By including a fiber optic fiber in each side of the connector, the fiber optic fibers could act as an alignment indicator.

Within the bundles, the fibers would be arranged such that when the fiber optic fibers were in alignment the capillary tubes would also be in alignment. By attaching the distal end of a fiber optic fiber contained within one bundle to a light source and attaching the distal end of a second fiber optic fiber contained within the second bundle to a light detector the fiber optic alignment indicator would be enabled. When light is provided to the distal end of one fiber and is detected at the distal end of the second fiber this indicates that the fiber optic fibers are precisely aligned. The capillary tubes that are in a fixed relation to the fiber optic fibers would then also be aligned. This alignment system would be very highly accurate because the light would only pass through the fiber optic fibers only if they were precisely aligned.

The simplest example of a manifold would be a connector that channels the contents from two capillary tubes to one capillary tube. One embodiment of this system is shown in FIG. 10. A first ferrule 65 contains two capillary tubes 57, 58 and one plugged capillary 56. The second ferrule 69 contains one capillary tube 63 and two plugged capillaries 62 and 61. A washer 60 is located between the two ferrule ends 65 and 69. The cut out 67 of the washer 60 would be in the shape of a V with the width of each leg of the V as wide as the diameter of the inner bore of the capillary tube with the greatest bore width.

When the manifold is assembled, ferrule end 65 is aligned end to end with ferrule end 69 with washer 60 located between the two sleeve ends. The two capillary tubes 57 and 58 funnel fluid into the top of the V in cut out 67 and the fluid would flow down into the point of the V where the single capillary 63 would receive this flow. In this manner the fluid in two tubes would be combined into a single tube.

The washer can be adapted to combine more than two tubes. Additional legs could be added to channel the fluid from a greater number of tubes into a single tube or multiple tubes in an opposing ferrule.

An alternative means to achieve the manifold function can be realized by recessing the ends of the capillary tubes in one ferrule from the end of that ferrule. The fluid would exit the capillary tubes and be pressure driven to the inner bore of the other capillary.

A schematic of the connector functioning as a fluid router is shown in FIG. 11. Two ferrule sections 70 and 80 are shown. Ferrule 70 contains a plugged capillary 71, and six radial fibers 72–77. One of the radial fibers is a capillary tube 77, the others are five plugged capillaries 72–76. Ferrule 80 contains a central plugged capillary 81 and six radial fibers 82–87. All of the radial fibers are capillary tubes. When the capillary tubes are of the same diameter, close packing is possible and highly recommended. Close packing of fibers on opposite sides of a valve leads to good fluid communication between opposite sides of a valve, without leakage or cross-contamination and aids in alignment of opposing capillaries.

As initially shown, the single capillary tube 77 in ferrule 70 is aligned with capillary tube 83 on ferrule 80. This allows fluid communication between the two capillary tubes 77 and 83. The other ends of capillary tubes 82, 84–87 in ferrule 80 would be blocked by plugged capillaries 72–76. Ferrule 80 could then be rotated by 1/12 of a turn clockwise. This would align capillary 77 in between capillaries 87 and 82 and would act as a closed valve for all positions. Ferrule 80 could then be rotated by a further 1/12 turn clockwise. This would align capillary tube 77 in ferrule 70 with capillary tube 82 in ferrule 80. Fluid communication between capillary tube 77 and capillary tube 82 is now possible. All the other capillary tubes in ferrule 80 are blocked by plugged capillaries in ferrule 70. By further subsequent rotations of ferrule 80 each of capillaries 82–87 could be brought into fluid communication with capillary 77 in ferrule 70.

With reference to FIG. 11a ferrule 70 is seen to contain plugged capillaries 71, 73, 74 and 75. On the other hand, capillary tubes 72, 76 and 77 are each open and may carry different reagents or samples. Ferrule 70 abuts ferrule 80 which has one plugged capillary 81 and open capillaries 82, 83, 84, 85, 86 and 87. When ferrules 70 and 80 are brought into an abutting relationship, the three capillaries 72, 76 and 77 and ferrules 70 may distribute fluid among the six capillaries in ferrule 80 by selective rotation of ferrule 70 with respect to ferrule 80.

Some of the uses for the present invention are illustrated by the following examples:

EXAMPLE 1

Injector

Figure 12:
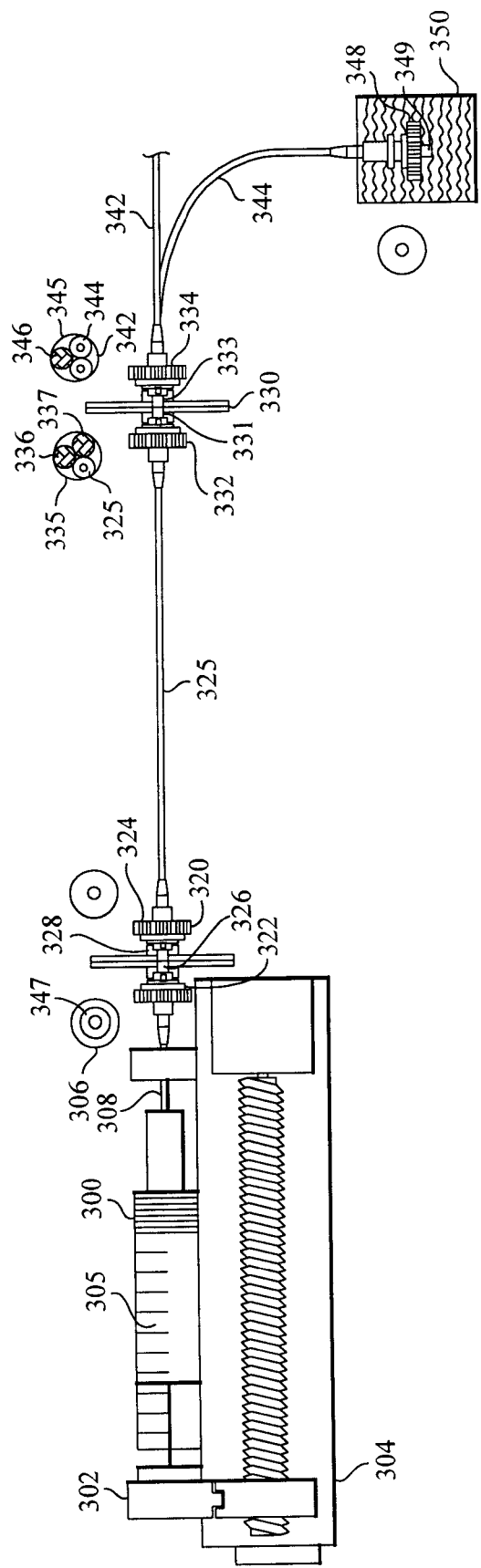
FIG. 12 is a plan view of a number of connector members of the type shown in FIG. 1 used for a macroscale injector injecting fluid through a microscale capillary tube.

As is illustrated in this example, the connector described above is adaptable for acting as an interface between macroscale devices, such as syringe pumps or injectors and microscale capillary tubes. FIG. 12 shows an injector apparatus. In this drawing, the connectors are pictured with the fastener cut away to reveal the interior of the associated ferrules. Representations of the ferrule face are pictured above each connector member.

In this embodiment, the injector is comprised of syringe 300 with a plunger 302 controlled by controller 304. The needle 308 of the syringe 300 terminates in ferrule 326 of connector member 322. A representation of the end of the ferrule 306 shows that the end of the needle 347 is a macroscale tube of up to 1 mm or more in diameter. The second connector member 324 contains a single microscale capillary tube 325. Capillary tube 325 extends from second connector member 324 and the opposite end of the length of capillary 325 terminates in ferrule 331 of connector member 332. Ferrule 331 contains a triplet packing of fibers shown in icon 335 which shows the capillary tube 325 and two plugged capillaries or fiber optic fiber ends 337 and 336. Ferrule 331 is in alignment with ferrule 333 of connector member 334. Ferrule 333 also contains triplet packing of fibers shown in icon 345. Terminating at the face of ferrule 333 are three fibers, capillary tube 344, capillary tube 342 and plugged capillary 346. Ferrule 333 would be rotated such that the bores of capillary tube 325 and capillary tube 344 were in alignment. Capillary tube 344 terminates at ferrule 349 attached to the optional connector member 348. This member is mounted on reservoir 350 with the capillary tip submerged.

The controller 304 could withdraw plunger 302 forming a vacuum that would draw fluid from reservoir 350 through capillary tube 344 through capillary tube 325 and into barrel 305 of syringe 300.

Sleeve 333 could then be rotated such that the inner bore of capillary 342 was aligned with the inner bore of capillary tube 325. Controller 304 then can depress plunger 302 forcing fluid through needle 308, into capillary tube 325 and into capillary tube 342. This system allows injections of determined amounts of fluid to be introduced into a flow stream.

EXAMPLE 2

Injector with Fluid Router

Figure 13:
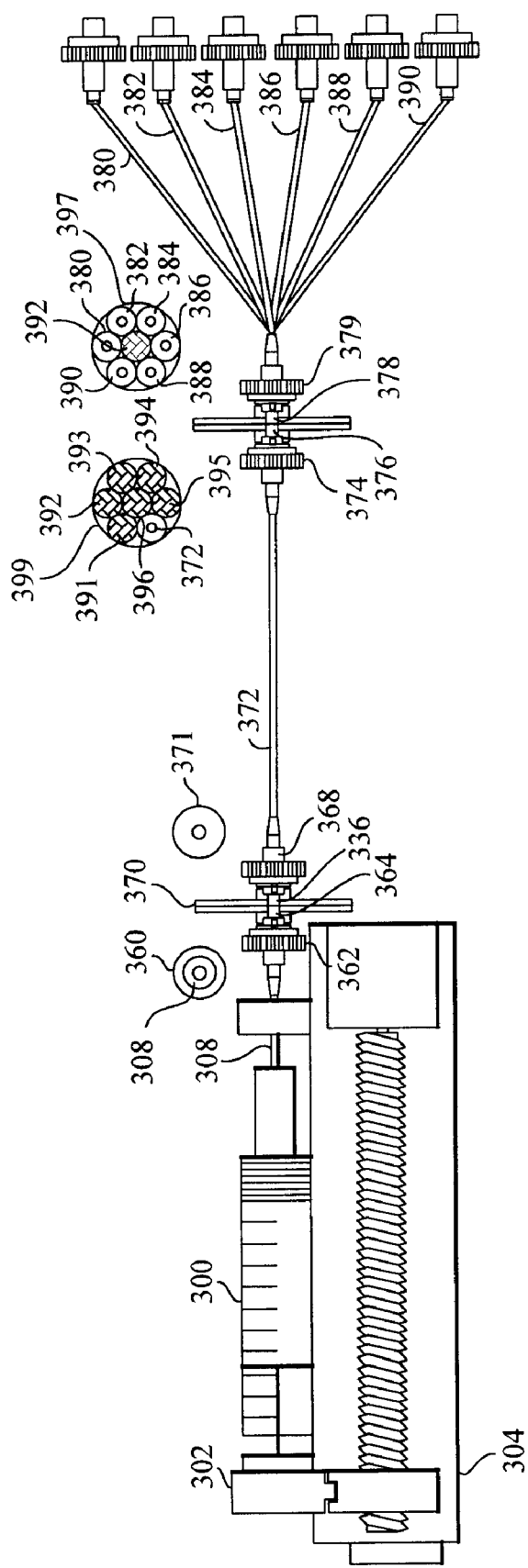
FIG. 13 is a plan view of the injector of FIG. 12 with an additional connector of the type shown in FIG. 1 functioning as a fluid router.

Once the basic injector has been developed, the connector members allow for a number of expanded functions. FIG. 13 demonstrates how the previously described injector can be expanded to include a fluid router. Like the previous apparatus, a controller 304 operates a syringe 300. The controller can depress plunger 302 forcing fluid into needle 308. Needle 308 terminates at ferrule 364 of connector 370. Fluid is transferred into capillary tube 372 located in ferrule 336.

The distal end of capillary tube 372 terminates at ferrule 376. The end of ferrule 376 is pictured at icon 395. Capillary tube 372 is the sole capillary tube within the bundle of fibers in ferrule 376. The bundle contains 7 fibers, with one fiber surrounded by six other fibers. Capillary tube 372 is packed with plugged capillaries 391–396. Ferrule 376 is in alignment with ferrule 378. Ferrule 378 also contains 7 fibers, a central plugged capillary 392 around which is packed six capillary tubes, 380, 382, 384, 386, 388, and 390. As pictured, capillary tube 372 in ferrule 376 is in alignment with capillary tube 384 in ferrule 378. All the other capillary tubes in ferrule 378 are blocked by the plugged capillaries in ferrule 376.

By rotating ferrule 376 one-sixth turn counter-clockwise, capillary tube 372 would be aligned with capillary tube 386. By performing subsequent one-sixth rotations of ferrule 376, capillary tube 372 could sequentially be brought into fluid communication with each of the six capillary tubes in ferrule 378. Thus the fluid from syringe. 300 could be directed to any of six capillary tubes affixed within ferrule 378. The capillary tubes contained within ferrule 378 then could be connected to a variety of analytical equipment. One or more of the capillary tubes could be connected to a reagent or wash reservoir. This injector could withdraw liquid from a reservoir attached to one of these lines and then could route the fluid into the other capillary tubes.

EXAMPLE 3

Sample Loading and Unloading

Figure 14:
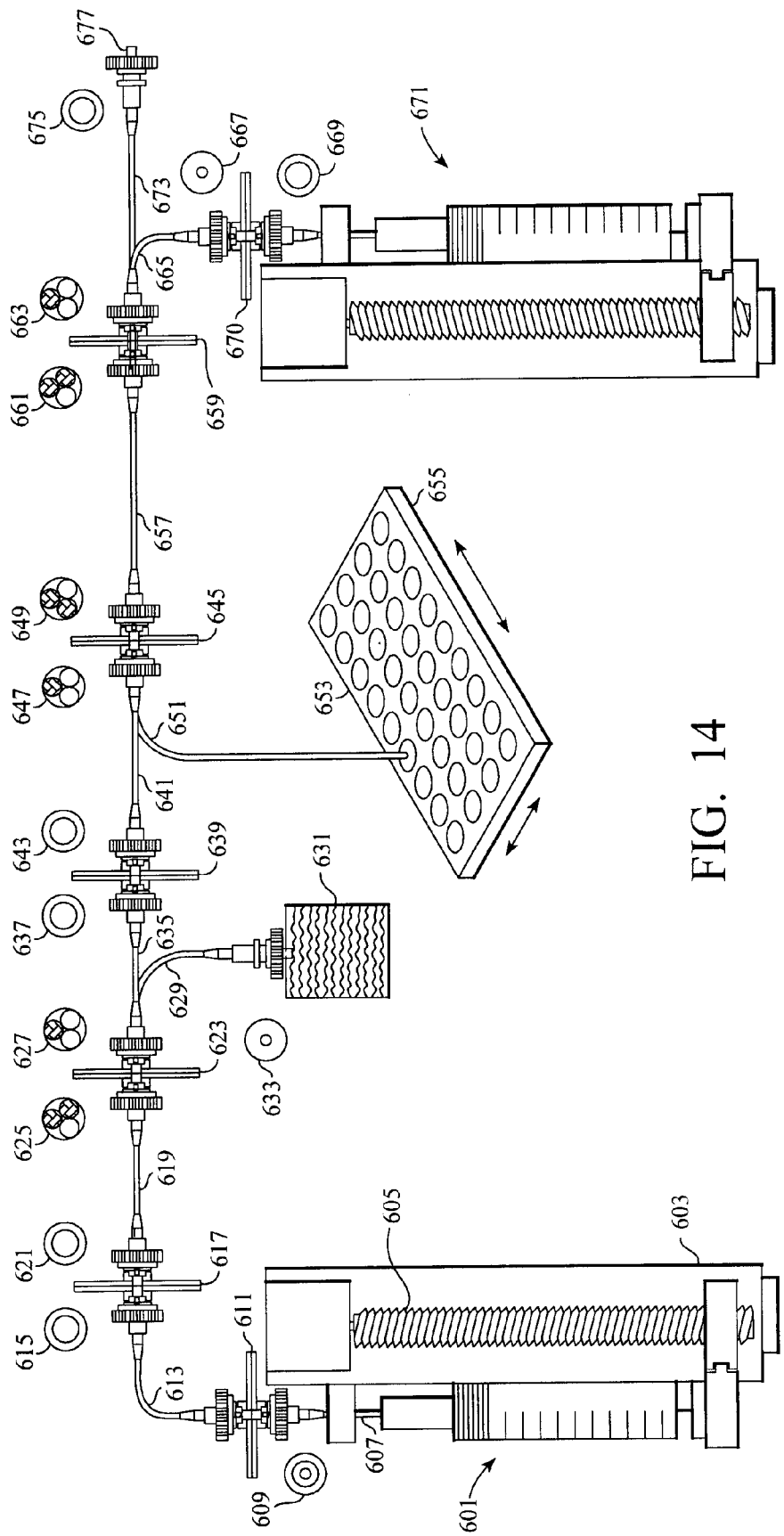
FIG. 14 is a plan view illustrating a sample loading and unloading apparatus using connectors of the type illustrated in FIG. 1.

With reference to FIG. 14, a first automated syringe pump 601 is operated by a microstepper motor 603 controlled by an electronic controller, not shown, driving a very fine screw 605 linked to the plunger of the syringe. The syringe has a barrel 607 whose cross section is shown by the icon 609 and is connected to adapter 611. The opposite side of the adapter 611 is connected to a first capillary storage section 613 having a known volume. This storage section is optional. The cross section of the storage capillary is shown by the icon 615. The capillary storage section is connected to an adapter 617 which links the first capillary storage section to a second capillary storage section 619 whose cross section is shown by the icon 621. The second capillary storage section, like the first section, has a known storage volume. The capillary storage section is bundled with two fibers which are plugged capillaries, as indicated by icon 625, showing the cross section of the three fibers, one of which is unplugged and is the capillary 619. The three fibers are linked to adapter 623 in the manner previously described with reference to FIG. 1, forming a first two-to-one branching valve 623. The output side of the branching valve has a cross section shown by icon 627 with two unplugged capillaries and one plugged capillary. One of the branches is capillary 629 having a cross section indicated by icon 633 and leading to a fluid reservoir 631. This reservoir contains a supply reagent which is to be injected into the system using the first syringe pump 601. The second output member of the branching valve 623 is the capillary storage section 635 having a cross section indicated by icon 637 and joined to adapter 639. Once again the capillary storage section 635 holds a known volume of fluid which may be pumped to other sections.

The adapter 639 joins a fourth storage capillary, having a cross section indicated by icon 643 to a second two-to-one branching valve 645 having an input section indicated by the icon 647. The icon 647 shows one plugged capillary section and two unplugged sections. One of the unplugged sections is the storage capillary 641 while the other is a capillary 651 in order to communicate with a plurality of wells 653 in the movable microtiter plate 655. The microtiter plate moves in X, Y and Z directions to bring the wells 653 into fluid communication with the tip of capillary 651. The output of the branching valve 641 is a fixed volume storage capillary 657 which is connected to a two-to-one branching valve 659. The output of the two-to-one branching valve 645 has a cross sectional shape indicated by the icon 649, with two plugged capillaries and one open capillary. Icon 661 has a similar configuration for the input side of branching valve 659. On the other hand, the output side of branching valve 659 has two open capillaries and one plugged capillary, indicated by icon 663. One of the capillaries 665 leads to the second syringe pump 671 via an adapter 670 with the input side having a cross sectional shape indicated by icon 667 and an output capillary having a cross sectional shape indicated by icon 669. The output is affixed to the barrel of the second syringe 671. The second output of valve 659 is a capillary of known volume 673 which terminates in a ferrule 677 which is linked to the main process flowstream which utilizes samples which have been loaded onto the microtiter plate 655 and then unloaded.

As may be seen from FIG. 14, samples may be drawn from reservoir 631 and pumped in known volummetric quantities by the first automated syringe pump 601 into storage capillaries 613, 619, 635, 641 and 657. The portion of sample in 657 may be pumped by means of the second pump 671 into capillary 651 for loading of the microtiter plate 655.

In withdrawing sample from the microtiter plate, the second pump 671 may be used to draw sample from a well to the storage capillary 657 and then the first pump used to push sample into the storage capillary 673 for advancement into the main process stream. In this manner, samples may be loaded from the microtiter plate, or other device such as microchip reservoir, and then withdrawn by the push-pull action of the first and second pumps. Alternatively, samples could be deposited into a microtiter plate, onto the surface of a microarray, or into a microchip for further processing or analysis.

An alternate embodiment can use a series of pairs of valves, such as 645 and 659, with a series of sampling capillaries, i.e. 651, to produce a series of samples if each pair of valves is separated by a capillary of fixed length. In an extension of this embodiment, the second pump 671 could use a fluid router, as shown in FIG. 13, to sequentially or simultaneously withdraw multiple samples from a microtiter plate or other source of sample. This will increase throughput for high throughput applications.

EXAMPLE 4

Nanoscale PCR

Figure 15:
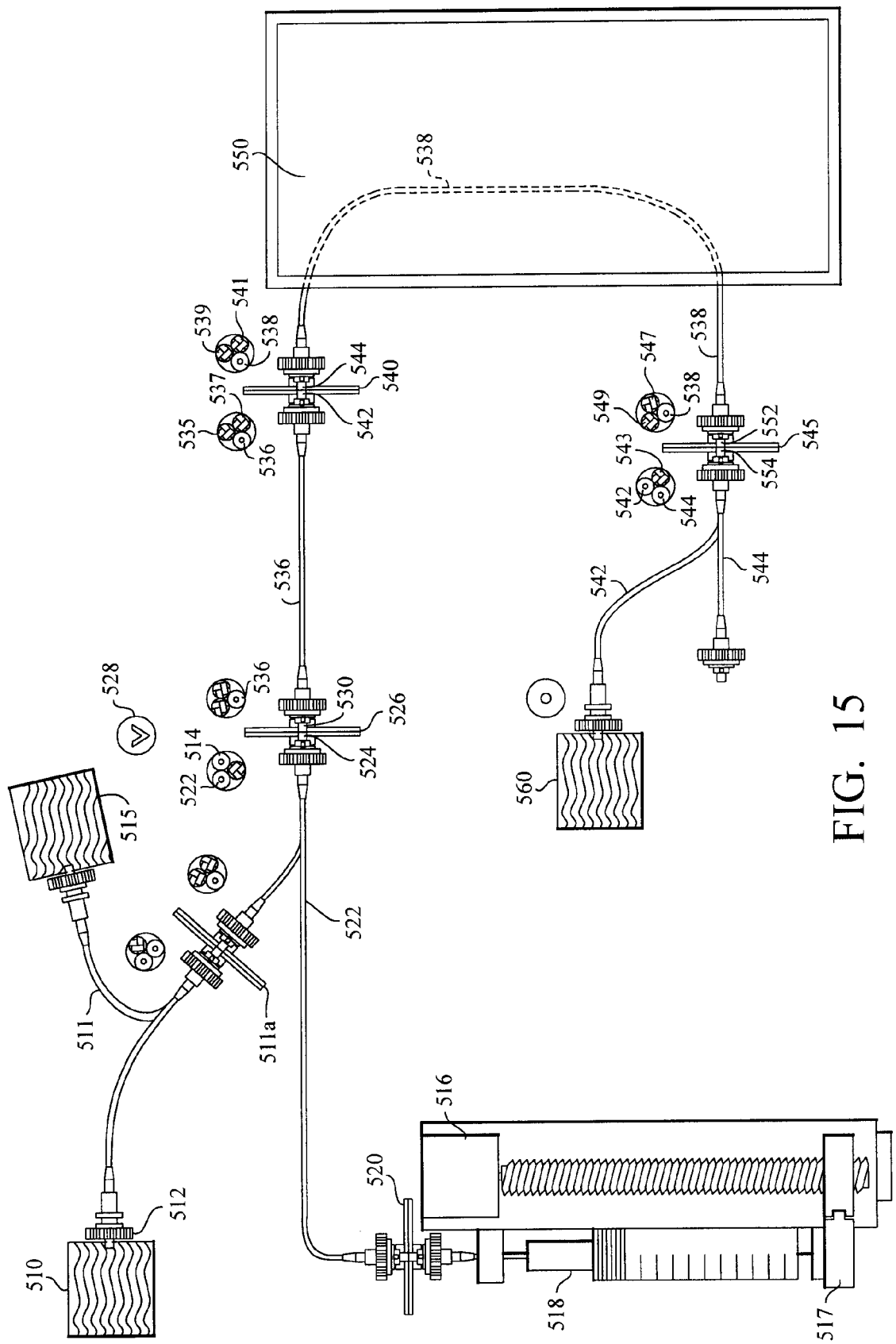
FIG. 15 is a plan view illustrating a nanoscale PCR apparatus using connectors of the type illustrated in FIG. 1.

The system described with reference to FIG. 15 can be utilized to create a system for performing the polymerase chain reaction (PCR) on a nanoscale level requiring from a few microliters to as little as a fewnanoliters of total reaction volume. Although this example shows PCR for a single DNA sample, the apparatus may be combined with the apparatus of the prior example so that multiple samples can be handled. While this example shows an implementation for PCR, alternate embodiments are applicable to other biochemical and chemical reactions, including those that use only a single temperature.

The basic idea for a nanoscale reaction system is adaptable to executing biochemical and chemical reactions on a very small scale. To perform this reaction, the length of capillary would be encased within a thermocycling heat pump or temperature-controlled device. The capillary tubes connecting into the length of capillary tube could deliver reagents for PCR in one of the input capillary tubes and a sample of DNA in the other input capillary. As shown in FIG. 14, the capillary inputs could originate in a microtiter plate. These would be combined into the single length of capillary tube and the two ends of the tube would be closed. The polymerase chain reaction would then take place as the thermocycling apparatus would then undergo the multiple cycles of timed temperature changes required for the reaction. The following description defines a device for executing this procedure.

The PCR reaction requires combination of two fluids, the PCR reaction mixture and the DNA sample. In this system, the PCR reaction mixture, containing the DNA polymerase, nucleotides, and a buffer mixture would be contained in pressurized reservoir 510. Adapter 512 is fastened onto the side of reservoir with adapter 512 bringing capillary tube 514 into fluid communication with the fluid in reservoir 510.

The DNA sample could be introduced through use of an injector. Injector syringe 518 would be automatically controlled by a motor 516 driven by a controller that would actuate the injector by depressing the plunger 517, introducing samples of DNA into the reaction mixture. A series of samples of DNA could have loaded into capillary 522 if the loading system described above were inserted into capillary 522. Adapter 520 would act as an interface between macroscale syringe 518 and microscale capillary tube 522.

Capillary tube 514 and capillary tube 522 would terminate at ferrule 524 on adapter 526. The second member of adapter 526 contains ferrule 530. Between the ends of ferrule 524 and ferrule 530 is washer 528, shown in a sectional icon. Washer 528 has a V shaped cut out. The inner bores of capillary tube 514 and capillary tube 522 align with the top legs of the V shaped cut out. The inner bore of capillary tube 536 aligns with the bottom of the cut out. The pressure from pressurized reservoir 510 and injector 518 would drive the fluids through the system and into capillary tube section 536.

Capillary tube 536 has a distal end that terminates at ferrule 542. Affixed within ferrule 542 is a set of three fibers, capillary tube 536 and two plugged capillaries, 535 and 537. Ferrule 542 is in facing alignment with ferrule 544. Inside ferrule 544 is affixed capillary tube 538 and plugged capillaries 539 and 541. When properly oriented, the end of capillary tube 536 and the end of capillary tube 538 are in alignment and fluid can flow from into tube 538. At the opposite end of capillary tube 538 is adapter 545. Capillary 538 terminates at ferrule 552. Affixed within ferrule 552 is capillary 538 and two plugged capillaries 549 and 547. Aligned facing ferrule 552 is ferrule 554. Ferrule 554 contains two capillary tubes, 544 and 542 and one plugged capillary 543.

After capillary tube 538 is filled with the reaction mixture and DNA sample, ferrule 542 can be rotated one-third turn, which will align the relatively non-rotating ends of capillary 536 with a plugged capillary 541. The second end of capillary tube section 538 can also be sealed by rotating ferrule 554 until plugged capillaries 549 and 547 block capillary tubes 542 and 544 and plugged capillary 543 blocks capillary tube 538. Capillary tube 538 would then be sealed on both ends. Chemistry could then be performed in capillary tube 538. Capillary tube section 538 is encased within thermal cycling apparatus 550. Apparatus 550 would then undergo temperature cycles to effect the polymerase chain reaction. When the reaction had completed, ferrule 542 could be rotated to again have capillary tubes 536 and 538 align. Ferrule 554 could be rotated so that capillary 538 aligned with capillary 544. The contents of the reaction tube could then be pumped from capillary tube 538 into capillary tube 544 which could lead to a DNA analysis apparatus. After capillary tube 538 had been emptied, ferrule 554 could be again rotated to align capillary tube 538 with capillary tube 542. At the same time, capillary 511 is aligned with capillary 514 and capillary 536 and capillary 538 through adapters 511a, 526 and 540. Capillary tube 542 leads to wash solution reservoir 560. Applying pressure on reservoir 560 will flush the reaction capillary 538, as will capillaries 536 and 514, into waste container 515 via capillary 511.

EXAMPLE 5

Capillary Electrophoresis DNA Detection

Figure 16:
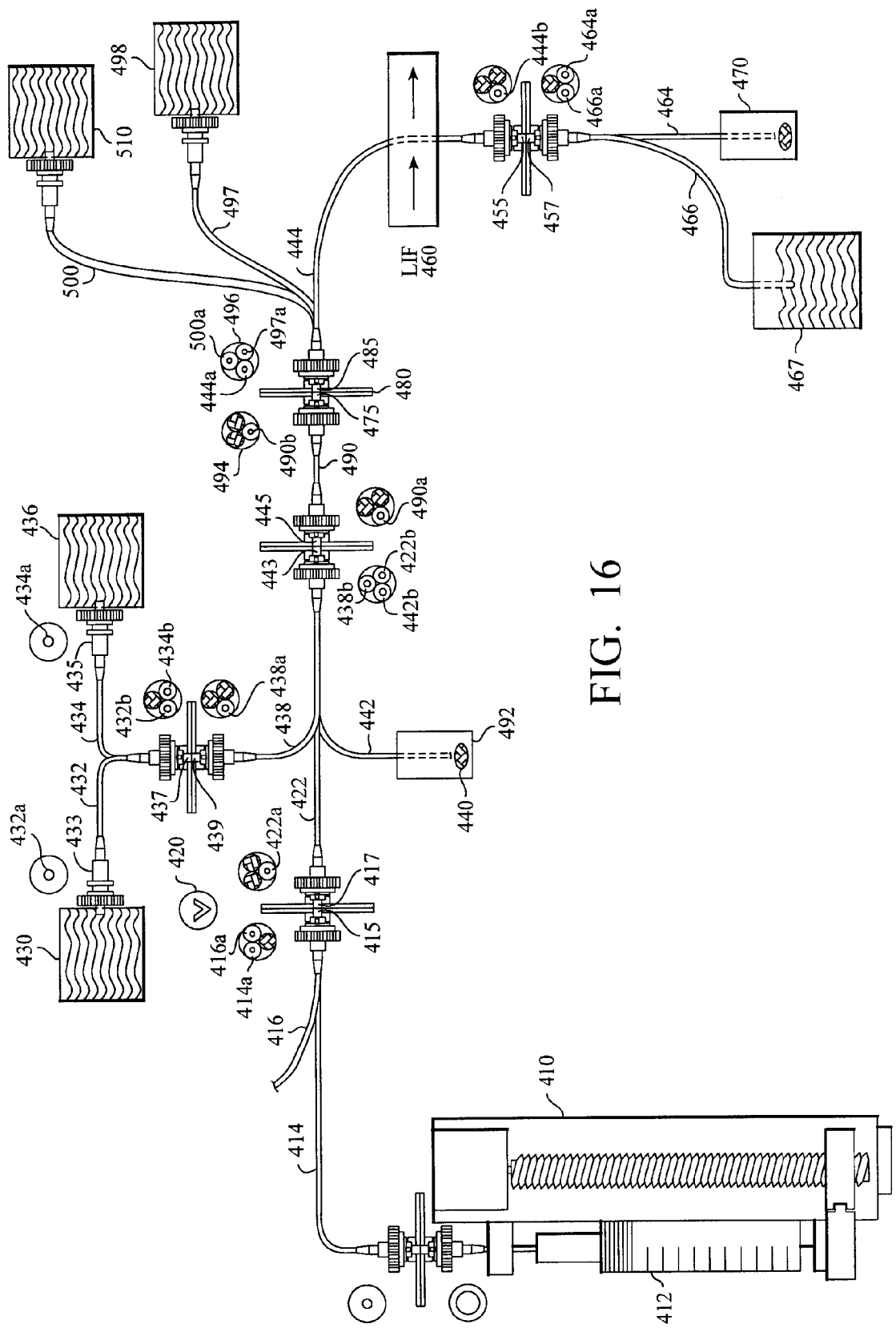
FIG. 16 is a plan view illustrating a system with capillary electrophoresis and laser induced fluorescence to detect DNA using connectors of the type illustrated in FIG. 1.

The capillary tubes described in the present invention are adaptable to equipment for the separation and analysis of chemicals and biopolymers, such as nucleic acid sequences. In FIG. 16, one embodiment of this system is shown. Although this example shows capillary electrophoresis for a single sample, the apparatus may be combined with the apparatus of Example 3 so that multiple samples could be handled. While this example shows capillary electrophoresis, alternate embodiments encompass other separation methods, such as microbore high pressure chromatography, gas chromatography, ion chromatography and mass chromatography.

For capillary gel electrophoresis, the first step in this process requires filling a capillary tube with a separation matrix. The separation matrix is kept in a pressurized reservoir 430 connected by adapter 433 to capillary tube 432, having a cross-section 432a shown in the icon above adapter 433. The end of this capillary tube is brought into fluid communication with capillary tube 438. The matrix will then flow through sample injection capillary tube 490 which is aligned with the capillary tube 438 to the end of the tube which is aligned with the end of capillary tube 444. See the cross sections near ferrules 443 and 445, as well as near ferrules 475 and 485. The opposite end of this tube 444b is aligned with an end of capillary tube 466 which conducts the displaced contents of tube 466 to a waste receptacle 467. See cross sections 444b and 466a near ferrules 455 and 457, respectively.

After capillary tube 444 has been filled with the separation matrix, the DNA sample and denaturant are moved into sample injection capillary 490. Syringe 412 controlled by controller 410 injects a fluorescently labeled DNA sample into capillary tube 414. Denaturant is introduced through capillary tube 416. The ends of these two tubes, corresponding to cross-sections 414a and 416a, terminate at ferrule 415. Abutting ferrule 415 is ferrule 417 containing single capillary 422. Between ferrules 415 and 417 is a washer 420 with a V shaped cut out. Fluid from capillary tube ends, corresponding to cross sections 414a and 416a, flow into the legs of the V and are combined at the point of the V into an end, corresponding to cross section 422a, of capillary tube 422. An alternative embodiment uses a ferrule with capillary tubes 414a and 414b recessed, as described. The sample and denaturant then flows through capillary 422 to ferrule 443 which has been rotated such that end 490a is aligned with end 422b of capillary tube 422 and the combined DNA and denaturant mixture are loaded into sample loading capillary 490. Ferrule 475 terminates capillary 490 and abuts ferrule 485 associated with separation capillary 444 and waste delivery capillary 497. When the sample injection capillary 490 is loaded, capillary end 490b is aligned with capillary 497a. Excess sample may be diverted into waste container 498 through waste capillary 497 from ferrule 485. If pressure injection is desired, the sample in the loading capillary 490 may also be advanced by pressure into separation capillary 444 toward ferrule 455, which, together with ferrule 457, is open to capillary 466 in communication with the waste reservoir 467. Icons 494 and 496 indicate that the loading capillary 490 may be switched between the reaction capillary 444 and a waste delivery capillary 497, leading to waste reservoir 498.

With the DNA sample and denaturant loaded into capillary tube 490, the sample is ready to be electrophoretically separated. Ferrule 443 is rotated so that end 490a aligns with end 442b of capillary tube 442. Ferrule 475 is rotated so that the loading capillary 490 communicates through ferrule 475 to the separation capillary 444 through ferrule 485. End 442a contains an electrode 440 in a reservoir 492 for introducing electric potential, i.e. voltage, into the capillary tube. The reservoir 492 is filled with a matrix which contains a conducting buffer, such as TBE (Tris, Boric acid, EDTA) or Tris-TAPS. At the other end of capillary tube 444, end 444b is aligned with end 464a of tube 464. This tube is also filled with a conducting buffer and terminates an electrode 470. Current will then flow from electrode 440 to electrode 470 through the buffer in capillary tube 442, through the denatured DNA sample in loading capillary 490, through the matrix in capillary tube 444 and then pass through the buffer in capillary tube 464 and into the electrode 470. The DNA will migrate through the separation matrix, with the smaller DNA fragments moving more quickly than the larger DNA fragments. DNA fragments, as they are moved by the voltage will be drawn past laser induced fluorescence apparatus 460. This apparatus provides laser light of a known frequency perpendicular to the DNA stream, causing the labeled DNA to fluoresce. The fluorescence is then detected by a detector.

After the separation and detection are complete, the sample loading capillary 490 may be purified with fluid from a wash reservoir 436 flowing under pressure through ferrule 437, through capillary 438, into loading capillary 490 and then to the waste delivery capillary 497, flowing into waste reservoir 498. Similarly, any remaining fluid in capillary 444 may be diverted through ferrules 455 and 457 into waste reservoir 467.

To load another sample, the loading capillary 490 is configured by alignment of ferrules 445, 443, 417 and 415 to receive fluid from sample capillary 414. An experiment may now proceed as previously described. It can be readily seen that by combining the sample loading system described in FIG. 14 with the separation method that multiple samples may be run in a single separation to achieve greater multiplexing.

To replace the matrix after an experiment or series of experiments, ferrule 457 is rotated to have end 444b of capillary tube 444 align with end 466a of capillary tube 466. Ferrule 475 is rotated so that the end of capillary tube 490b aligns with end 444a of capillary tube 444. Ferrule 443 is rotated so that the end of capillary tube 490a aligns with end 438b of capillary tube 438. Ferrule 437 is rotated so that the end of capillary tube 438a aligns with end 434b of capillary tube 434. The other end 434a of capillary tube 434 is in fluid communication with wash solution in pressurized wash reservoir 436. Wash solution would then be driven through capillary 434, through capillary 438, through capillary 490, through capillary 444, and into capillary tube 466 where it would be transferred into waste reservoir 467. After washing of the matrix from the capillary tubes, the matrix could be refilled, as described above.

From the above description, it may be seen that the capillary valve, connector and router of the present invention provide a method for performing chemical reactions or performing separations of chemical reactions. The above examples shows that reactants for a chemical reaction or measurement may be placed in a plurality of capillary tubes having ends which terminate in a closely spaced pattern within a first ferrule. The opens ends of the tubes face in the same direction. Selected reactants may be merged into a single reaction capillary which is movable among the plurality of capillary tubes. The reactants can be combined by moving the reaction capillary tube among the various capillary tubes among the plurality of tubes. Alternatively, a flow conduit defined in a washer or the like placed between the plurality of capillary tubes and the single tube may provide the desired flow channel. If the plurality of capillary tubes is arranged in a first ferrule and the single capillary tube is in a second ferrule, abutting the first ferrule, movement of one ferrule with respect to the other will bring the single capillary tube into selective communication with desired capillaries among the plurality of capillary tubes.

The preferred arrangement of capillary tubes within a ferrule is shown by the examples of FIGS. 17a–17e. FIG. 17a shows an outer ring of fifteen capillaries surrounding an intermediate ring of nine capillaries which, in turn, surrounds an inner ring of three capillaries. FIG. 17b shows an outer ring of twelve capillaries surrounding an intermediate ring of six capillaries which, in turn, surround a single capillary. FIG. 17c shows an outer ring of nine capillaries surrounding an inner ring of three capillaries. FIG. 17d shows an outer ring of six capillaries surrounding a single capillary. FIG. 17e shows a rectangular array of capillaries. In each case, capillaries are tangent to other capillaries. To achieve tangency, the capillaries are preferably the same size so that close packing can be achieved. Fibers are interchangeable with capillaries but, if difficulty is encountered in obtaining optical fibers which are the same size as capillaries, plugged capillaries are used. The geometries illustrated in FIGS. 17a–17e are illustrative examples of close packing. Other geometries including linear arrays of capillaries exist.

EXAMPLE 6

Nanoscale Sequencing

In this next example, the capillary connectors are again used as valves to close and isolate sections of capillary tube. These sections may be used as reaction chambers. Each of these sections of capillary tubes may be included in a temperature-regulating chamber, whereby the contents of the capillary section may be exposed to a selected sequence of temperatures, effecting the desired reaction. A number of such capillary tubes sections (each having associated values) to allow the capillary section to be temporarily sealed enclosed with a temperature-regulating chamber could be arranged in a single processing stream. After each reaction is complete, a new combination of reagents could be added into the flow stream. In this way a reaction that requires multiple steps of addition of reagents followed by incubation or temperature cycling could be effected in a single flow stream. In addition, the contents within each capillary section may be small volume boluses of liquid isolated by air or an inert liquid. The inert liquid is selected such that the reaction mixture will not combine with the inert liquid, allowing the liquid to serve as an isolating agent.

Figure 18:
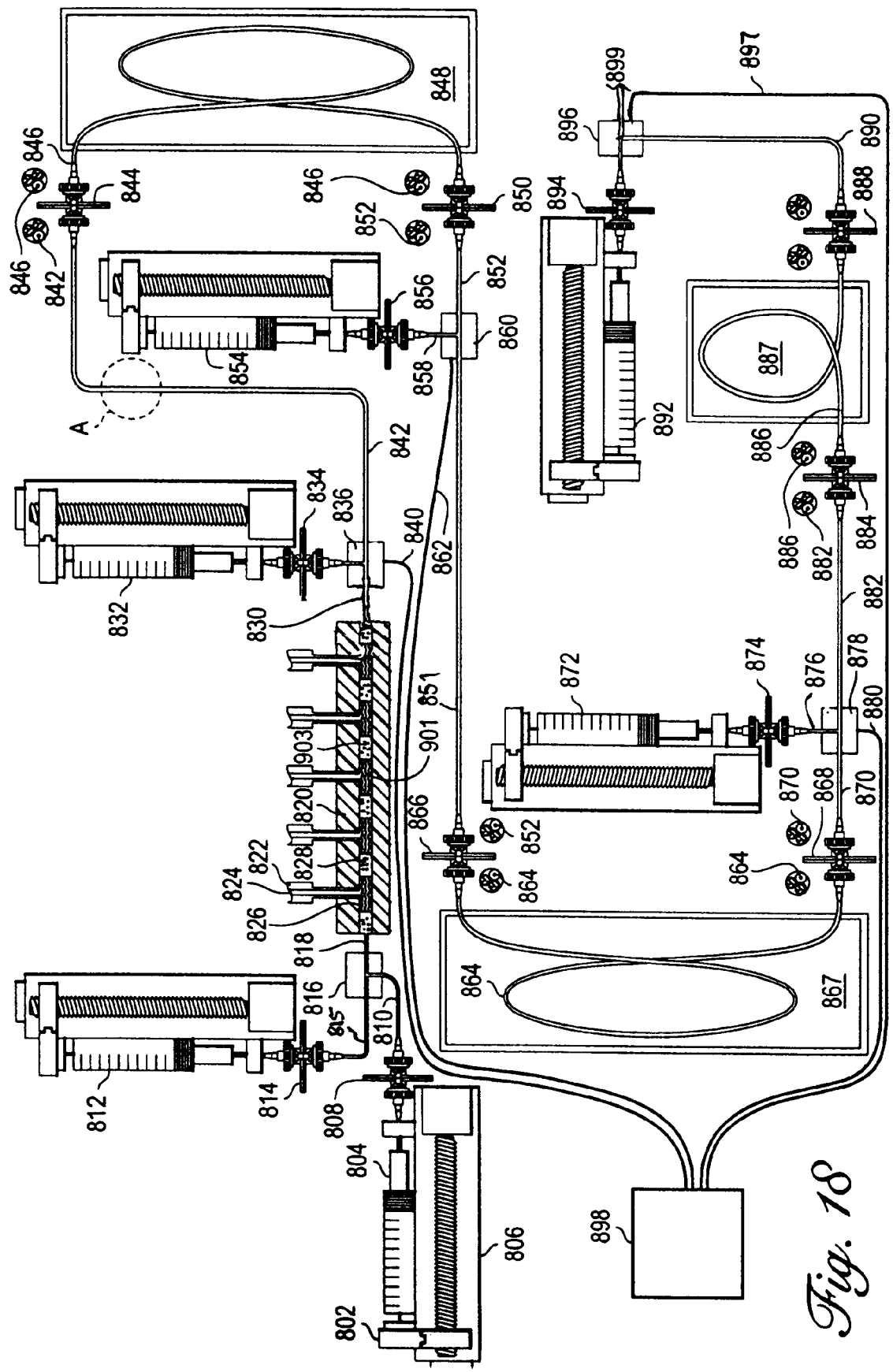
FIG. 18 is a schematic layout of a microfluidic apparatus using connectors of the type illustrated in FIG. 1 to integrate a sample loading and unloading; nanoscale PCR, nanoscale ExoI/SAP reactions, with nanoscale cycle sequencing reactions.

In the present example, this type of system is illustrated in FIG. 18. The system, as described, is used to produce a chain termination sequencing reaction mixture from plasmid isolates. In a preferred embodiment, this procedure requires PCR amplification of the plasmid insert, enzymatic clean up of the PCR reaction products and cycle sequencing to sequence the amplified DNA insert. In one embodiment, the samples are moved through the capillary as boluses separated by a flowing material selected so that the material does not mix with the reaction mixture.

With reference to FIG. 18, an injector 802 having an injection barrel 804 and an associated stepper control 806 is filled with an initial component of the reaction mixture, such as a liquid buffer. The stepper control 806 provides a fine control of the injection volume, allowing injection volumes of less than 1 µL, and as low as 0.1 nL. Connector 808 connects injection passageway of the injector to capillary tube section 810. Capillary tube 810 terminates in a passageway through substrate 816.

Substrate 816 is comprises of two substrate layers (e.g. glass, ceramic, plastic, etc.) bonded together. Microchannels are patterns into one of the two layers before the layers are bonded. The capillary tubes may be inserted into the openings in the side of substrate 816 such that the volume from the capillaries flow into the microchannels in substrate 816. Each of the combining substrates has two microchannels that liquid flows into from injectors or the processing stream. Each substrate has a single outflow microchannel.

A second injector 812 is connected by a connector 814 to a capillary tube section 815 that terminates in substrate 816. Injector 812 is filled with FluorInertJ (Amersham, N.J.), air or another gas, or other gas or liquid that would not mix or diffuse into the boluses of reaction liquid. Injectors 812 and 802 alternate, injecting small amounts of liquid into microchannels of substrate 816. An injection of the liquid reaction mixture component is followed by the injection at the inert, flowable liquid produces a flow stream containing boluses of reaction mixture separated by a volume of the inert fluid. At a distal area in the flow stream suction may be used to remove the air displaced from the flow stream. The flow stream flows from combining substrate 816 onto capillary 818.

Capillary 818 flows into sample injection substrate 820, which is shown in cross-section in an enlarged view. Capillary 818 is joined to injection substrate 820 with a fluid tight seal such that the flow stream flowing from capillary 818 may flow into channel 828 in sample injection substrate 820. The reaction mixture boluses 826, 901 that are moved through the flow stream are positioned such that samples, such as nucleic acid containing samples (e.g. plasmid isolates), may be injected into the boluses. Inserted into ports in the sample injection substrate 820 are injectors 822 having injection passageways 824. The injector is pictured as having five injection ports. However, in practice 8 or 12 injection ports compatible with 96 well microplate well spacing may be preferred. Nucleic acid samples may be injected into the boluses using electro-kinetic injection, pressure injection, or other injection means. The samples are injected into the fluid boluses. The boluses 826, 901 are separated by a flowing separation media 828, 903.

Once the samples are injected into the flow stream, the flow stream moves from sample injection substrate 820 to capillary 830, which is secured by a fluid at one end to injection substrate 820 and at a second end to combining substrate 836. Injector 832 is connected to combining substrate 836 by connector 834. Injector 832 injects a preset quantity of polymerase chain reaction reagent mixture (i.e. DNA polymerase, dNTPs, buffer, primers) into bolus of nucleic acid containing reaction mixture. An electronic monitor 840 controlled by electronic control 898 monitors the fluid flow through combining substrate 836. Electronic monitor 840 may detect a change in the optical, electrical, or chemical flow in the flow stream to determine when the bolus containing the nucleic acid sample is aligned with the injector. Electronic control may be electronically linked to injector 832 to coordinate the timing of the injection into the reaction mixture boluses. As the PCR reagent mixture is injected into the sample boluses the flow stream flows into capillary section 842.

Figure 19:
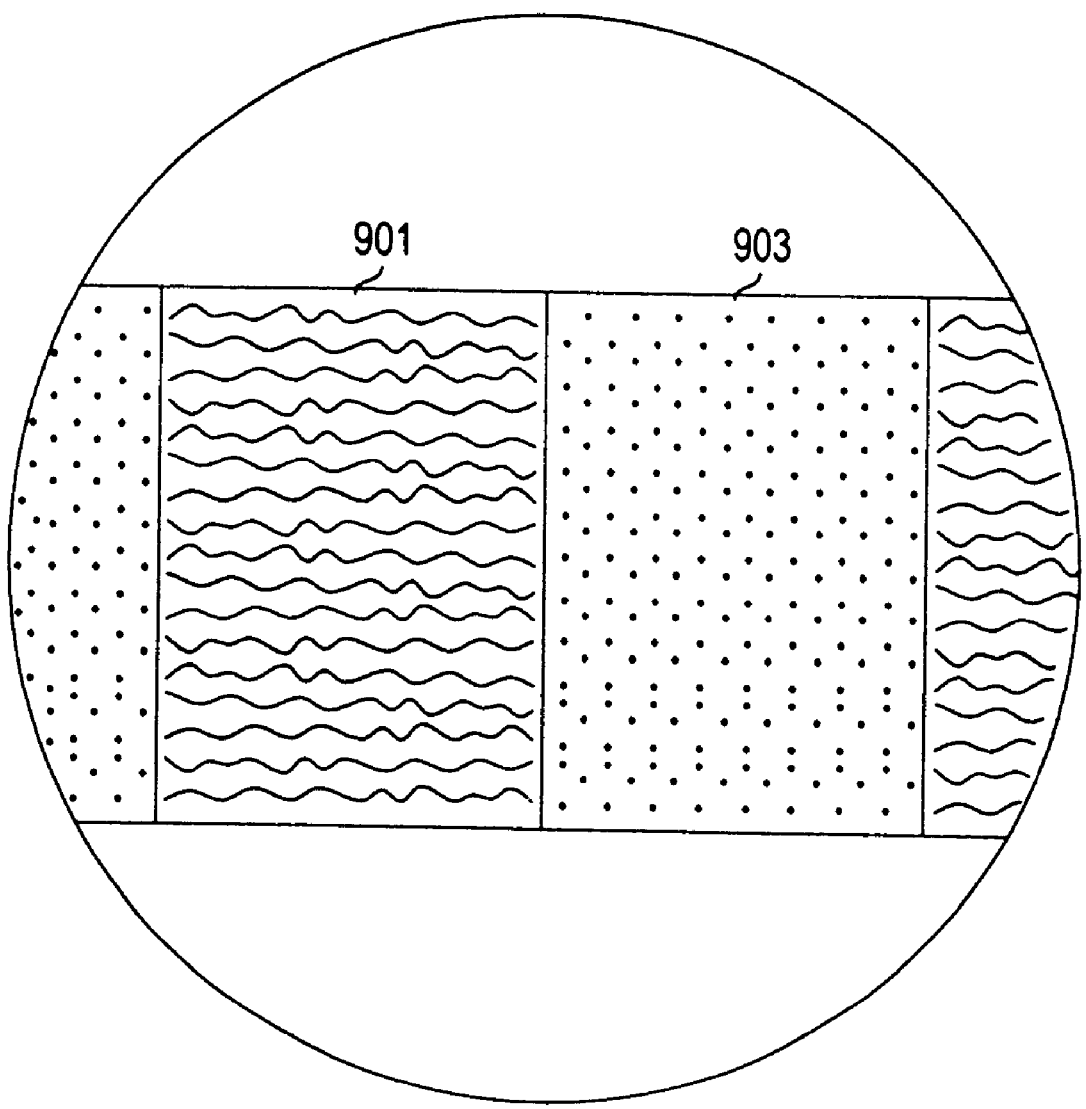
FIG. 19 is a depiction of a series of sample boluses separated by fluid.

The fluid within the capillary tube section A is illustrated in FIG. 19. The capillary contains a volume of reaction mixture 901 separated by the flowable, inert fluid 903. Fluid 903 effectively isolates reaction mixture bolus 901 within the capillary.

Returning to FIG. 18, capillary tube section 842 terminates at connector 844. Connector 844 holds the ends of capillary tubes 842 and 846 in mutually biased alignment. At a distal end capillary tube section 846 is attached by connector 850 to capillary tube section 852. Capillary tube section 846 is contained within temperature regulating chamber 848. The capillary section 846 may be sealed by rotating the connectors 844, 850 such that the ends of the capillary tube section 846 do not align with capillary sections 842 and 852, respectively. The connectors 844, 850 hold the capillary in a spring biased ferrule that is both simple to rotate and produces a biasing force that seals the end of the capillary tube section. A capillary tube section may be effectively isolated by rotating the ends of the capillary tube section out of alignment with the abutting capillary tubes. Temperature regulation chamber 848 may expose capillary tube 846 to an environment that promotes a chemical reaction. In the present example, the combined reaction mixtures in the flow stream contain PCR reagents and a nucleic acid containing sample. Within temperature regulating chamber 848, capillary tube section 846 may be exposed to repeated incubation cycles (e.g. one interval at a melting temperature to create single stranded DNA, a second interval at a lower annealing temperature, and a third interval at an extension temperature for each cycle). The temperature regulating chamber may use circulating air, water, Peltier devices, or other methods to effect rapid temperature changes. The thin walls of the capillary and low capillary volume allow rapid temperature changes and more rapid reaching of equilibrium temperatures. Following completion of the amplification, connector valves 844, 850 may be rotated such that the ends of capillary tube section 846 are again aligned with capillary tubes 842, 852. The reaction mixtures, having completed an PCR amplification reaction, are moved into capillary tube section 852.

Capillary tube section 852 terminates in combining substrate 860. Combining substrate 860 allows a set of Acleanup@ reagents (e.g. shrimp alkaline phosphatase and exonuclease I to digest PCR reagents) be added to each reaction mixture bolus. Injector 854 is connected to injection capillary 858 by connector 856. Injector 854 contains a mixture of enzyme reagents that digest the reagents of the previous reaction, but do not affect the amplified nucleic acid fragments. As seen before, monitor 862, controlled by electronic control 898 determines when the reaction mixture is in position for injection of the clean-up reagents. Following the injection of the clean-up reagents, the flow stream flows into capillary tube section 851, which is secured at one end to combining substrate 860 and is secured at another end to connector 866.

Connector 866 connects capillary section 851 with capillary section 864. Most of the length of the capillary section 864 is contained within incubator 867. The distal end of capillary tube section is linked to capillary tube section 870. As before, capillary tube section 864 may be temporarily sealed by rotation connectors 866, 868 such that the ends of capillary tube section 864 are not aligned with the ends of capillary tube sections 851, 870. When the ends of capillary section 864 are sealed, the reaction mixtures within the tubes may be incubated at a selected temperature. For the clean up reaction, the reaction mixtures would be incubated at a first temperature at which the enzymes digest the unreacted PCR reagents, followed by a second temperature incubation in which the clean up enzymes are heat inactivated. Following the completion of this reaction the ends of capillary tube section 864 are again brought into alignment with capillary tube sections 851 and 870 and the reaction mixture flow stream may be pumped into capillary section 870.

Capillary section 870 terminates in combining substrate 878. As before, an injector 872 is joined by a connector 874 to a capillary segment 876. This injector contains chain termination amplification reagents for cycle sequencing for the sequencing reaction. The capillary segment 876 terminates in combining substrate 878. Monitor 880 in conjunction with electronic control 898 monitors the flow stream and instructs injector 872 to inject the chain termination amplification reagents when the reaction mixture boluses are positioned in line with the injection flow stream. Following injection of the amplification reagents, the flow stream flows into capillary section 882, which is secured into the combining substrate.

Capillary tube segment 882 is connected at a distal end to capillary tube segment 886 by connector 884. Capillary tube segment 886 is connected at a distal end to capillary tube segment 890 by connector 888. By rotating connectors 884, 888, the capillary tube segments may be brought out of line with the ends of capillary tube segments 882, 890. Capillary segment 886 is contained within temperature regulating chamber 887. With the ends of capillary segment 886 sealed, the cycle sequencing reaction may take place within each isolated reaction mixture bolus within the capillary segment. The capillary tube segment may then be exposed to selected incubation temperatures. For cycle sequencing, this would require brief denaturation to separate strands of DNA followed by a longer annealing/extension temperature. After a selected number of these cycles, connectors 884 and 888 could again be rotated so that capillary tube section 886 is aligned with the adjoining capillaries. The contents of capillary 886 may then be drawn into capillary tube section 890.

Capillary tube section 890 terminates in combining substrate 896. Injector 892 is coupled to the combining substrate 896 by connector 894. This injector contains buffers or other reagents needed for preparing the amplified fragments for analysis. It may be required to dilute the prepared reaction mixtures prior to analysis. Monitor 897 controlled by electronic control 898 monitors when the reaction mixture is positioned to receive the injection. Following the injection into each reaction mixture bolus, the flow stream leaves the combining substrate 896 and flows into capillary 899. This capillary may transport the reaction mixture bolus to an analytical device, such as a capillary electophoresis device or a mass spectrometer. Ideally, the analytical device would allow perform extremely rapid analysis or perform parallel analysis of the isolated samples, allowing for more rapid analysis of the reaction products generated by the described system.

Although the system is illustrated with a single flow stream, it is possible to arrange a number of capillaries in parallel flow streams to further increase throughput. The incubators, electronic control, and other system elements could be used with multiple flow streams.

What is claimed is:

1. A method for performing chemical reactions comprising:
   providing reactants for a chemical reaction in a plurality of capillary tubes, each capillary tube having an end that terminates at spaced locations on a first connector face;
   merging the reactants in at least two of the plurality of capillary tubes into a reaction capillary tube having a first and second open end, wherein said first open end terminates on a second connector face joined to said first connector face in a face-to-face biased alignment;
   effecting a reaction of the reactants within the reaction capillary tube; and
   removing the contents of the reaction capillary tube after a chemical reaction has occurred.

2. The method of claim 1 further defined by connecting at least one capillary tube among said plurality of capillary tubes to a macroscale apparatus.

3. The method of claim 1 wherein the plurality of capillary tubes terminate in a first ferrule and the single reaction capillary tube terminates in a second ferrule abutting the first ferrule, the method further defined by moving the first ferrule relative to the second ferrule thereby bringing the reaction capillary into fluid communication with a selected one of the plurality of capillary tubes.

4. The method of claim 1, wherein said merging step includes providing between said first connector face and said second connector face a gasket, said gasket channeling fluid from at least two of said plurality of capillary tubes into the reaction capillary tube.

5. The method of claim 1 wherein said merging step includes sequentially moving liquid from a first capillary tube in said plurality of capillary tubes into the reaction capillary tube and subsequently moving liquid from a second capillary tube in said plurality of capillary tubes into the reaction capillary tube.

6. The method of claim 1 further comprising analyzing contents of the reaction tube after effecting a reaction.

7. The method of claim 6, wherein said analyzing step includes moving a reacted liquid in the reaction capillary tube into an analyzing capillary which has an end terminate on a third connector face;
   wherein the second open end of the reaction capillary terminates on a fourth connector face;
   wherein the third and fourth connector faces are held in mutually biased alignment such that liquid may flow from the reaction capillary into the analyzing capillary.

8. The method of claim 7 wherein said analyzing includes optically analyzing liquid in the analyzing capillary.

9. The method of claim 7 wherein said analyzing step includes making a conductivity measurement.

10. The method of claim 1 wherein the step of effecting a reaction includes exposing the reaction capillary to thermal cycles.

* * * * *